US010082509B2

(12) United States Patent
Dukan et al.

(10) Patent No.: US 10,082,509 B2
(45) Date of Patent: Sep. 25, 2018

(54) METHOD FOR LABELING SPECIFICALLY LIVING AND BACTERIA COMPRISING THE USE OF MODIFIED MONOSACCHARIDE COMPOUNDS

(71) Applicants: CENTRE NATIONAL DE LA RECHERCHE SCIENTIFIQUE (CNRS), Paris (FR); UNIVERSITE D'AIX-MARSEILLE, Marseilles (FR)

(72) Inventors: Sam Dukan, Marseilles (FR); Boris Vauzeilles, Sceaux (FR); Aurelie Baron, Bois de Boulogne (FR); Jordi Mas Pons, Rubi (ES)

(73) Assignees: CENTRE NATIONAL DE LA RECHERCHE SCIENTIFIQUE, Paris (FR); UNIVERSITE D'AIX-MARSEILLE, Marseilles (FR)

( * ) Notice: Subject to any disclaimer, the term of this patent is extended or adjusted under 35 U.S.C. 154(b) by 0 days.

(21) Appl. No.: 15/028,155

(22) PCT Filed: Oct. 29, 2014

(86) PCT No.: PCT/EP2014/073252
§ 371 (c)(1),
(2) Date: Apr. 8, 2016

(87) PCT Pub. No.: WO2015/063173
PCT Pub. Date: May 7, 2015

(65) Prior Publication Data

US 2016/0238609 A1 Aug. 18, 2016

(30) Foreign Application Priority Data

Oct. 30, 2013 (EP) .................................... 13190794

(51) Int. Cl.
*G01N 33/58* (2006.01)
*C12Q 1/02* (2006.01)
*C12Q 1/04* (2006.01)
*G01N 33/569* (2006.01)

(52) U.S. Cl.
CPC ............... *G01N 33/58* (2013.01); *C12Q 1/02* (2013.01); *C12Q 1/04* (2013.01); *G01N 33/56911* (2013.01)

(58) Field of Classification Search
None
See application file for complete search history.

(56) References Cited

U.S. PATENT DOCUMENTS

| | | | | |
|---|---|---|---|---|
| 9,057,093 B2 * | 6/2015 | Fovet | C12Q 1/04 |
| 9,181,204 B2 * | 11/2015 | Leibl | C07D 249/06 |
| 9,181,575 B2 * | 11/2015 | Fovet | C12Q 1/06 |
| 9,492,473 B2 * | 11/2016 | von Maltzahn | A61K 31/715 |
| 9,493,809 B2 * | 11/2016 | Dukan | C12Q 1/04 |
| 2005/0142629 A1 | 6/2005 | Kahne et al. | |
| 2008/0268468 A1 | 10/2008 | Wong et al. | |
| 2014/0363817 A1 * | 12/2014 | Dukan | C12Q 1/04 435/6.11 |
| 2016/0238609 A1 * | 8/2016 | Dukan | C12Q 1/02 |
| 2017/0030908 A1 * | 2/2017 | Dukan | C12Q 1/04 |

FOREIGN PATENT DOCUMENTS

| | | | |
|---|---|---|---|
| WO | 2009108807 A1 | 9/2009 |
| WO | 2013107759 A1 | 7/2013 |
| WO | WO 2015/063173 A1 * | 5/2015 |

OTHER PUBLICATIONS

Jaipuri A et al.: "Synthesis and Quantitative Evaluation of Glycero-D-manno-heptose Binding to Concanavalin A by Fluorous-Tag Assistance", Angewandte Chemie International Edition, vol. 47, No. 9, Jan. 18, 2008, pp. 1707-1710.

Reiko Sadamoto et al: "Bacterial Surface Engineering Utilizing Glucosamine Phosphate Derivatives as Cell Wall Precursor Surrogates", Chemistry—A European Journal, vol. 14, No. 33, Nov. 17, 2008, pp. 10192-10195.

S. Muller-Loennies et al.: "A monoclonal antibody against a carbogydrate epitope in lipopolysaccharide differentiates Chlamydophila psittaci from Chlamydophila pecorum, Chlamydophila pneumoniae and Chlamydia trachomatis", Glycobiology, vol. 16, No. 3, Nov. 3, 2005, pp. 184-196.

International Search Report dated Jan. 21, 2015, corresponding to International Patent Application PCT/EP2014/073252.

* cited by examiner

*Primary Examiner* — Nita M. Minnifield
(74) *Attorney, Agent, or Firm* — Ladas & Parry LLP; Malcom J. MacDonald

(57) ABSTRACT

The invention relates to a method for labeling specifically living bacteria of a given category of Gram negative bacteria in a sample comprising bacteria, the method including the steps of:

a) incubating the bacteria of the sample with at least one modified monosaccharide compound having a first reactive chemical group capable of reacting with a second reactive group, so that a monosaccharide residue bearing the first reactive group is incorporated into the polysaccharides of the outer membrane of such bacteria, and
b) contacting the modified monosaccharide residue incorporated within the outer membrane of the bacteria, with a labeling molecule having a second reactive group.

25 Claims, 6 Drawing Sheets

(A)

1 (Ia)

(Ib-1)

5
6
7
8
9
10a, R=Ts
10b, R=Ms
11
Ia-1
Ia-1'

METHOD FOR LABELING SPECIFICALLY LIVING AND BACTERIA COMPRISING THE USE OF MODIFIED MONOSACCHARIDE COMPOUNDS

This application is a 371 of PCT/EP2014/073252, filed on Oct. 29, 2014, which claims priority to European Patent Application No. 13190794.1, filed Oct. 30, 2013.

The present invention concerns a method for labeling of living bacteria comprising species-specific metabolic polysaccharide labeling in incorporating modified monosaccharide compounds in the polysaccharides (especially LPS or CPS) of the outer membrane of Gram negative bacteria. The present invention provides more particularly a method allowing specific labeling especially of *Legionella pneumophila* using precursors of endogenous monosaccharides, which are specifically present within the LPS of the outer membrane of this bacterium.

WO 2013/107759 discloses a method of labeling living bacteria, more particularly, Gram negative bacteria. The method essentially consists in incorporating in the membrane of said bacteria by assimilation an analog of monosaccharide compound of the ulosonic acid type modified so that it bears a so-called first reactive chemical function such as azide (—$N_3$) or alkyne (—C≡CH) group thus enabling a reaction of this first reactive group with a molecule bearing the complementary reactive group especially through a so-called click chemistry reaction.

More particularly, it has been disclosed in WO 2013/107759 that such modified analogs of endogenous sugars comprising ulosonic acid or ulosonate residue are particularly advantageous in that such residues can be found in glycans of the bacterial membrane, especially LPS of all of the Gram negative bacteria, and moreover they can be directly assimilated in the same form into which they will be incorporated in the said glycans of the LPS of Gram negative bacteria.

Ulosonic acids (also called ketoaldonic acids, or aldulosonic acids) are monosaccharides of the ketose family, presenting a ketone function at C-2, and a carboxylic acid at C-1. Octulosonic and nonulosonic acids are found in diverse natural glycans, including different forms of bacterial glycans (especially LPS, capsular polysaccharide, glycoproteins). The biosynthetic pathway leading to the elaboration of these glycans generally involves the free ulosonic acid as an intermediate, which is then directly activated in the form of a CMP-sugar donor. All of the Gram negative bacteria LPS comprise a said ulosonate residues.

More accurately, the method disclosed in WO 2013/107759 is a method for specifically labeling living bacteria of a given category of bacteria in a sample comprising bacteria, the method comprising the steps of:

a) incubating said bacteria of said sample with at least one analog of a monosaccharide compound, said monosaccharide being an endogenous monosaccharide residue of glycans of the outer membrane of such given category of bacteria, the said endogenous monosaccharide residue comprising an ulosonic acid or ulosonate salt residue, the said analog of a monosaccharide compound being a modified monosaccharide substituted at a given position by a first reactive chemical group capable to react with a second reactive group of a labeling molecule, and b) contacting said bacteria with a said labeling molecule comprising a said second reactive group, for generating the reaction of said first reactive group of said analog residue incorporated within said glycans of the outer membrane of said living bacteria with said second reactive group of said labeling molecule.

Particularly, in WO 2013/107759 the said analog monosaccharide is a substituted ulosonic acid having one of the following formula (I') or an ulosonate salt thereof:

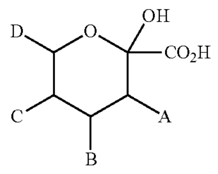

Wherein

A, B and C can be independently H, OH, $NH_2$, OH and $NH_2$ being substituted or not by protecting groups thereof, and D is an alkyl chain in $C_2$ to $C_4$, and at least one of A, B, C or D groups is substituted by a said first reactive group.

In WO 2013/107759, the said analog of monosaccharide incubated with the living bacteria in step a) and then incorporated within its outer membrane after assimilation by the bacteria, can be identical to the endogenous monosaccharide incorporated in the glycans chain of the outer membrane except it is modified only by substitution of the said first reactive group.

The goal of the present invention was to find out improved monosaccharidic compounds capable to be assimilated within Gram negative bacteria and incorporated in their LPS of their outer membrane presenting advantageous properties as to their specificity of incorporation in respect to the concerned category of bacteria and/or as to their greater capacity to penetrate within the cells bacteria and/or as to their greater easiness of chemical synthesis thereof.

According to the present invention, it has been found that it was possible to use in step a) a monosaccharide compound modified by the said first reactive group, said monosaccharide compound being different than the endogenous monosaccharide residue of polysaccharides of the glycans of the outer membrane of such bacteria, such as LPS or capsular polysaccharide (CPS), and then being nevertheless capable to penetrate and be incorporated in the outer membrane of wild type bacteria namely bacteria which are not deficient in the biosynthesis pathway of the corresponding endogenous monosaccharide.

According to the present invention, the said monosaccharide compounds being modified by the said first reactive group comprise precursors of endogenous monosaccharide in the biosynthetic pathway thereof. More particularly, the part of the compound molecule of such precursors of the present invention onto which the said first reactive group is substituted, is different than the endogenous monosaccharide residue incorporated in the glycans chain of the outer membrane but it is metabolized in a modified said endogenous monosaccharide residue incorporated in the glycans chain of the outer membrane as specified herein after, said endogenous monosaccharide being modified by said first reactive group.

More particularly, the present invention provides precursors of modified endogenous monosaccharides of the above formula I' disclosed and claimed in WO 2013/107759. Indeed, the modified precursors of the present invention are metabolized and converted during the incubation step a) into modified monosaccharides in the form of the same molecules as the endogenous monosaccharides residues of the glycans of the outer membrane of such bacteria except that it bears the said first reactive groups.

More accurately, the present invention provides a method for labeling specifically living bacteria of a given category of bacteria in a sample comprising bacteria, the method comprising the steps of:

a) incubating said bacteria of said sample with at least one modified monosaccharide compound comprising a first reactive chemical group capable to chemically react with a second reactive group, so that a monosaccharide residue bearing said first reactive group is incorporated into the polysaccharides of the outer membrane of such bacteria, especially into the LPS or CPS of the outer membrane of such bacteria, and b) contacting said modified monosaccharide residue incorporated within the outer membrane of the bacteria, with a labeling molecule comprising a said second reactive group, for generating the chemical reaction of said first reactive group of said monosaccharide residue incorporated within said outer membrane of said living bacteria with said second reactive group of said labeling molecule, resulting in a covalent link, characterized in that the said modified monosaccharide compound is a modified endogenous precursor of an endogenous ulosonic acid residue of the said polysaccharides of the outer membrane of said bacteria, said modified monosaccharide compound having the following formula (I), or a salt thereof:

I

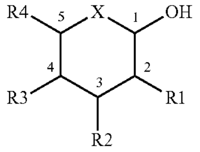

Wherein

X can be O, NH or S, preferably O and NH, more preferably O, and

R1, R2 and R3 can be independently H, OH, $NH_2$, OH and $NH_2$ being substituted or not by protecting groups thereof, preferably substituted by alkyl, hydroxyalkyl, acyl, formyl or imidoyl groups, and R4 is H or an alkyl chain in $C_1$ to $C_4$, each carbon being substituted or not by OH or $NH_2$ substituted or not by protecting groups thereof, preferably by alkyl, hydroxyalkyl, acyl, formyl or imidoyl groups, and at least one of X, R1, R2, R3 and R4 groups, preferably R1, R3 or R4, being substituted by a said first reactive group Ra.

The said chemical reaction between said first and second reactive groups results in a covalent link which in few examples can be a covalent coordination link in a metallic complex coordinated with ligands.

It must be understood that the said monosaccharide of said modified monosaccharide compound is an endogenous precursor (not modified) having a formula as formula (I) but without the said first reactive group. The said modified endogenous precursors of the present invention are easier to prepare chemically than a said modified endogenous monosaccharide residue of the ulosonic acid type of the said polysaccharides of the outer membrane of said bacteria while said modified endogenous precursors are metabolized in the bacterial cell and give rise to the assimilation within the outer membrane into a different form namely in the form of the said modified endogenous monosaccharide residue of polysaccharides of the outer membrane of the concerned bacteria.

Another advantage of these precursors of the present invention is that they don't comprise polar groups such as —COOH and therefore can penetrate within the bacterial cells more rapidly and/or more easily.

Another advantage of such precursors of the present invention is that they can be metabolized in several different modified endogenous monosaccharides present in respectively different serogroups or subspecies of a same species of bacteria as further specified herein after in connection with *Legionella pneumophila* species.

More particularly, it has been found that the said compound of above defined formula I can be converted during the assimilation process by the bacteria into a modified endogenous monosaccharide of the ulosonic acid type of the following formula I':

I'

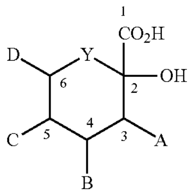

Wherein:

Y is O or NH such that R2=YH, Y being O when R2 is OH and Y is NH when R2 is $NH_2$;

A can be independently H, OH, $NH_2$, preferably H or OH, being substituted or not by protecting groups thereof, preferably substituted by alkyl, hydroxyalkyl, acyl, formyl or imidoyl groups, and B can be independently H, OH, $NH_2$, preferably OH or $NH_2$, being substituted or not by protecting groups thereof, preferably substituted by alkyl, hydroxyalkyl, acyl(Ac), formyl or imidoyl groups, and C is R1, and D is —CHR3-CXHR4.

Accordingly, in said modified precursor of formula I, R1, R2, R3 and R4 are such that they are comprised in Y, C and D of said modified endogenous monosaccharide of the ulosonic acid type of formula I' as above mentioned.

Such compound of formula (I) can be assimilated by a category of Gram negative bacteria and incorporated into the outer membrane of such bacteria in the form of a modified endogenous monosaccharide residue of glycans of the LPS of the outer membrane thereof, said endogenous monosaccharide residue comprising an ulosonic acid or ulosonate salt residue, the said first reactive group being after incorporation of said modified monosaccharide compound within said glycans of the outer membrane at a position which is a free group in said modified endogenous monosaccharide residue.

It has been found that the compounds of formula (I) can enter successfully in competition with the corresponding natural precursor provided it is used in high enough concentration, especially at a concentration of at least $10^{-5}$M, more particularly $10^{-5}$M to 1M.

More particularly, the incubation time at step a) is from 1 hr to 24 hr, preferably from 2 hr to 12 hr and the modified monosaccharide compound concentration is from $10^{-5}$M to 1M, for detecting a bacteria concentration preferably of no more than $10^{11}$ cell/ml, more particularly no more than $10^{9}$ cell/ml.

More particularly, for OH the protecting group can be preferably an alkyl, hydroxyalkyl, acyl or formyl group.

More particularly, for $NH_2$ the protecting groups can be selected among alkyl, hydroxyalkyl, acyl, formyl or imidoyl groups.

$NH_2$ can be protected by one or two protecting groups, especially one $CH_3$ group and one alkyl, hydroxyalkyl, acyl, formyl or imidoyl group. More particularly, in the above formula I, $NH_2$ groups can be in the form of N-acetyl (NHAc), or can be in the form of N-acetimidoyl (NHAm), N—(N-methylacetimidoyl), N—(N,N-dimethylacetimidoyl), N-formyl (NHFo), NH-hydroxybutanoyl (NH-Hb), and can be further N-methylated or not.

It is to be noted that the compounds of formula I and I' may be in equilibrium with compounds of the following formula II and III and respectively II' and III' as follows:

More particularly, said bacteria are chosen among *Acinetobacter baumanii, Bacteroides fragilis, Bartonella bacilliformis, Bartonella quintana* (*Rochalimaea quintana*), *Bartonella* spp. (*Rochalimaea* spp.), *Bordetella bronchiseptica, Bordetella parapertussis, Bordetella pertussis, Brachyspira* spp, *Brucella melitensis* (*sensu stricto*), *Brucella melitensis* biovar *Abortus* (*Brucella abortus*), *Brucella melitensis* biovar *Canis* (*Brucella canis*), *Brucella melitensis* biovar *Suis* (*Brucella suis*), *Burkholderia mallei* (*Pseudomonas mallet*), *Burkholderia pseudomallei* (*Pseudomonas pseudomallei*), *Chlamydophila psittaci* (*Chlamydia psittaci*), *Coxiella burnetii, Francisella tularensis* subsp. *Tularensis* (*"Francisella tularensis* subsp. *nearctica", Francisella tularensis* biovar *Tularensis, Francisella tularensis* type A), *Campylobacter fetus, Campylobacter jejuni, Campylobacter* spp, *Cardiobacterium hominis, Chlamydophlla abortus, Chlamydophlla caviae, Chlamydophlla felis, Chlamydophlla pneumoniae* (*Chlamydia pneumoniae*), *Edwardsiella tarda, Ehrlichia* spp, *Eikenella corrodens, Elizabethkingia meningoseptica* (*Flavobacterium meningosepticum, Chryseobacterium,*

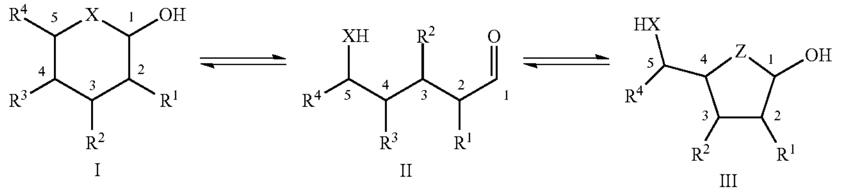

I II III

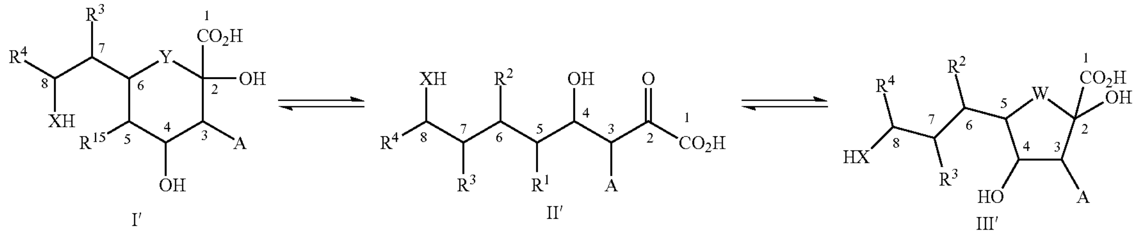

I' II' III'

W, Y, and Z being O or NH such that R1=WH, R2=YH and R3=ZH.

In step a), the said first reactive group is preferably substituted on a position of the said monosaccharide compound which comprises a free group in the said endogenous monosaccharide residue incorporated within said polysaccharide of the outer membrane of the bacteria. By "free group" is meant a position not engaged in a covalent bond within the said LPS.

The compound of formula (I) can be used for labeling Gram negative pathogens bacteria having at least one of the positions of an ulosonic acid or ulosonate residue free in their outer membrane LPS which can be selected among these later compounds are precursors of endogenous monosaccharides of the type of ulosonic acid or salt thereof which can be found interalia in the following genus of bacteria: *Legionella, Pseudomonas, Clostridium, Campylobacter, Acinetobacter, Vibrio, Listeria, Escherichia, Pseudoalteromonas, Sinorhizobium, Shigella, Yersinia, Schewanella, Salmonella, Providentia, Proteus, Tenacibaculum, Bacteroides, Bartonella, Bordetella, Brachyspira, Brucella, Burkholderia, Chlamydophlla, Coxiella, Francisella, Cardiobacterium, Edwardsiella, Ehrlichia, Eikenella, Elizabethkingia, Enterobacter, Enterococcus, Fusobacterium, Haemophilus, Helicobacter, Klebsiella, Leptospira, Morganella, Neisseria, Neorickettsia, Pasteurella, Plesiomonas, Porphyromonas, Prevotella, Providencia, Rickettsia, Streptobacillus, Treponema.*

*eningosepticum*), *Enterobacter aerogenes* (*=Klebsiella mobilis*), *Enterobacter cloacae, Enterobacter* spp, *Enterococcus* spp, *Escherichia coli, Francisella tularensis* subsp. *holarctica* (*"Francisella tularensis* var. *palaearctica*"), *Francisella tularensis* type B), *Fusobacterium necrophorum, Haemophilus ducreyi, Haemophilus influenzae, Haemophilus* spp, *Helicobacter pylori, Campylobacter pylori, Klebsiella oxytoca, Klebsiella pneumoniae, Klebsiella* spp, *Legionella bozemanae* corrig. (*Fluoribacter bozemanae*), *Legionella pneumophila, Legionella* spp, *Leptospira interrogans, Leptospira interrogans sensu lato* inclut *Leptospira alexanderi, Leptospira borgpetersenii, Leptospira fainei, Leptospira inadai, Leptospira interrogans, Leptospira kirschneri, Leptospira noguchii, Leptospira santarosai, Leptospira weilii, Morganella morganii* (*Proteus morganii*), *Neisseria gonorrhoeae, Neisseria meningitidis, Neorickettsia sennetsu* (*Ehrlichia sennetsu, Rickettsia sennetsu*), *Pasteurella multocida, Pasteurella* spp, *Plesiomonas shigelloides, Porphyromonas* spp, *Prevotella* spp, *Proteus mirabilis, Proteus penneri, Proteus vulgaris, Providencia alcalifaciens, Providencia rettgeri* (*Proteus rettgeri*), *Providencia stuartii, Providencia* spp, *Pseudomonas aeruginosa, Pseudomonas fluorescens, Pseudoalteromonas atlantica, Pseudoalteromonas distincta, Rickettsia* spp, excluding *Orientia* (*Rickettsia*) *tsutsugamushi, Rickettsia akari, Rickettsia canadensis, Rickettsia conorii, Rickettsia montanensis,*

*Rickettsia prowazekii, Rickettsia rickettsii* et *Rickettsia typhi, Salmonella enterica* subsp. *Arizonae* (*Salmonella arizonae, Salmonella choleraesuis* subsp. *arizonae*), *Salmonella enterica* subsp. *enterica* sérovar *Enteritidis* (*Salmonella enteritidis*), *Salmonella enterica* subsp. *enterica* sérovar Paratyphi A (*Salmonella paratyphi*), Paratyphi B, and Paratyphi C, *Salmonella enterica* subsp. *enterica sérovar Typhimurium* (*Salmonella typhimurium*), *Schewanella japonica, Shewanella putrefaciens, Shigella boydii, Shigella dysenteriae*, except type 1, *Shigella flexneri, Shigella sonnei, Streptobacillus moniliformis, Tenacibaculum maritimum, Treponema carateum, Treponema pallidum, "Treponema pertenue"* ("*Treponema pallidum* subsp. *pertenue*"), *Treponema* spp, *Vibrio alginolyticus, Vibrio cholerae, vibrio parahaemolyticus* (=*Beneckea parahaemolytica*), *Vibrio* spp, *Yersinia enterocolitica, Yersinia ruckeri, Yersinia pestis* and *Yersinia pseudotuberculosis.*

Preferably, the said modified monosaccharide compound is a compound having the formula (I) or a salt thereof wherein:

X is O, and

R1 is H, OH, $NH_2$, OH and $NH_2$ being substituted or not by said protecting group, and R3 is $NH_2$ substituted or not substituted by protecting group thereof, preferably Ac;

R2 is OH substituted or preferably not substituted by a protecting group thereof, and at least one of R1, R3 and R4 being substituted by a said first reactive group Ra.

More particularly, R4 is —$CH_3$, —$CH_2OH$ or —$CH_2NH_2$, these groups being substituted by said first reactive group Ra.

Preferably, said bacteria are Gram negative bacteria, comprising an endogenous monosaccharide residue within the LPS layer of its outer membrane and the above later compounds can be used for labeling of said bacteria, preferably selected among the following mentioned bacteria: *Legionella pneumophila, Vibrio alginolyticus, Acinetobacter baumannii, Pseudomonas fluorescens, Vibrio salmonicida, Tenacibaculum maritimum* (former *Flexibacter maritimus*), *Escherichia coli, Salmonella typhymurium, Schewanella japonica, Providencia stuartii, Pseudomonas aeruginosa, Yersinia ruckeri, Salmonella arizonae, Morganella morganii, Shewanella putrefaciens, Shigella boydii, Proteus vulgaris, Pseudoalteromonas atlantica, Pseudoalteromonas distincta, Sinorhizobium fredii, vibrio cholerae, Pseudoalteromonas atlantica, Vibrio parahaemolyticus, Campylobacter jejuni, Campylobacter coli, Clostridium botulinum* and *Yersinia enterocolitica.*

More particularly, the said modified monosaccharide compound is a compound having one of the following formulas (Ix-1) to (Ix-4), or a salt thereof:

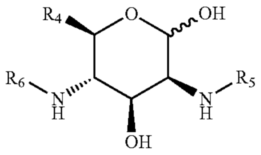

Ix-1

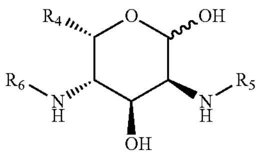

Ix-2

-continued

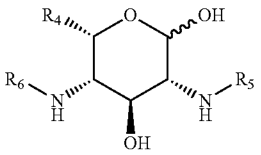

Ix-3

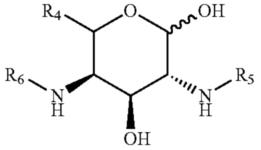

Ix-4

Wherein

R4 is H or an alkyl chain in $C_1$ to $C_4$, each carbon being substituted or not by OH or $NH_2$ substituted or not by protecting groups thereof, preferably by alkyl, hydroxyalkyl, acyl, formyl or imidoyl groups, R4 being preferably H, $CH_3$, $CH_2OH$ or $CH_2NH_2$ and R5, R6 can be independently alkyl, hydroxyalkyl, acyl, formyl or imidoyl groups, substituted or not, R5 and R6 being preferably an acyl (Ac), and at least one of R4, R5 and R6 groups being substituted by a said first reactive group.

More particularly, the said modified monosaccharide compound is a compound having the formula (I) or a salt thereof wherein:

X is O, and

R1 and R3 are $NH_2$ substituted or not substituted by protecting group thereof, and R2 is OH substituted or preferably not substituted by protecting group thereof, and R4 is substituted by Ra, Ra being a said first reactive group, the said first reactive group being preferably $N_3$, R4 being preferably $CH_3$, $CH_2OH$ or $CH_2NH_2$ substituted by Ra.

More particularly, the said modified monosaccharide compound is selected among the following compounds Ia and Ib:

compound Ia being a compound having the formula (I) wherein R1 and R3 are —NHAc, R2 is —OAc or preferably OH and R4 is $CH_2$—Ra, preferably —$CH_2$—$N_3$; and compound Ib being a compound having the formula (I) wherein R1 and R3 are —$NHCOCH_2Ra$, preferably Ra being $N_3$, R2 is —OAc or preferably OH and R4 is $CH_2OH$.

More particularly, said modified monosaccharide compound is a compound having one of the following stereoisomers formulae (Ia-1) to (Ia-4) and (Ib-1) to (Ib-4), or a salt thereof:

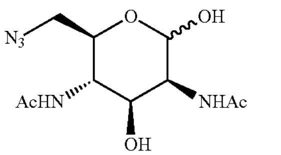

Ia-1

-continued

Ia-2

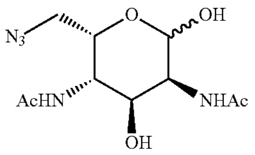

Ia-3

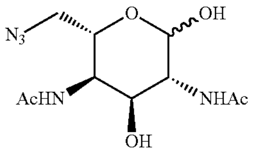

Ia-4

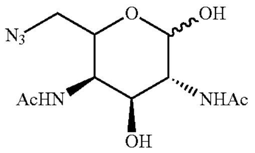

Ib-1

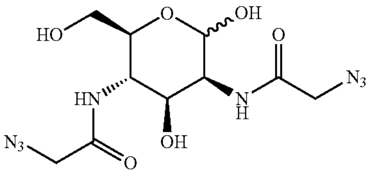

Ib-2

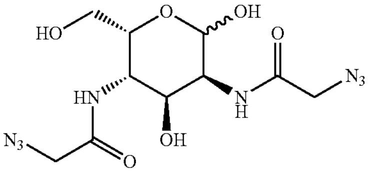

Ib-3

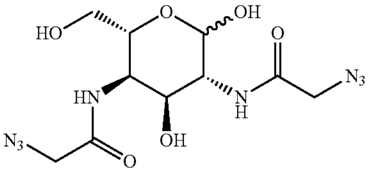

Ib-4

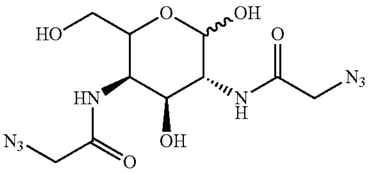

Formulae Ia-1 and Ib-1 are included into formula Ix-1.

The monosaccharide parts of compounds of formulae (Ix-1) to (Ix-4) are precursors of the following nonulosonic acid type endogenous monosaccharides of formulae Ic-1 to respectively Ic-5, namely:

(Ix-1) is a precursor of endogenous monosaccharide compounds of following formula (Ic-1) and (Ic-2);

(Ix-2) is a precursor of endogenous monosaccharide compound of following formula (Ic-3);

(Ix-3) is a precursor of endogenous monosaccharide compound of following formula (Ic-4); and (Ix-4) is a precursor of endogenous monosaccharide compound of following formula (Ic-5).

(Ic-1)=

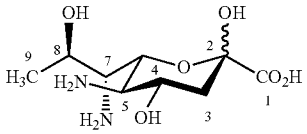

Leg (5,7-diamino-3,5,7,9-tetradeoxy-D-glycero-D-galacto-non-2-ulosonic acid), (Ib-6) can be found in *Legionella pneumophila, Vibrio alginolyticus, Acinetobacter baumannii, Pseudomonas fluorescens*, and *Vibrio salmonicida.*

(Ic-2)=

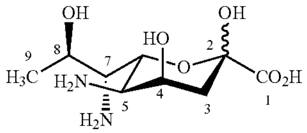

4eLeg (5,7-diamino-3,5,7,9-tetradeoxy-D-glycero-D-talo-non-2-ulosonic acid), (Ib-1) can be found in the LPS of *Legionella pneumophila* bacteria and in *Schewanella japonica.*

(Ic-3)=

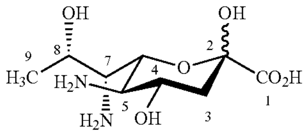

8eLeg (5,7-diamino-3,5,7,9-tetradeoxy-L-glycero-D-galacto-non-2-ulosonic acid), (Ib-2) can be found in *E. coli* strains, *Providencia stuartii, Pseudomonas aeruginosa, Yersinia ruckeri, Salmonella arizonae, Morganella morganii, Shewanella putrefaciens.*

(Ic-4)=

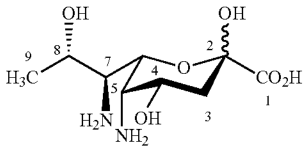

Pse (5,7-diamino-3,5,7,9-tetradeoxy-L-glycero-L-manno-non-2-ulosonic acid) (Ib-5) can be found in the O-antigen (LPS) of *Pseudomonas aeruginosa, Shigella boydii, Escherichia coli, Proteus vulgaris, Pseudoalteromonas atlantica, Pseudoalteromonas distincta, Sinorhizobium fredii*, and *Vibrio cholerae, Pseudoalteromonas atlantica* and cell wall of *Kribella* spp. 5 (Gram +) and *Actinoplanes utahensis* (Gram +) and LPS core of *Vibrio parahaemolyticus* and in flagellar glycoproteins of *Campylobacter jejuni, Campylobacter coli, Helicobacter pylori*, and *Clostridium botulinum*, and in the CPS of *Sinorhizobium* bacteria.

(Ic-5)=

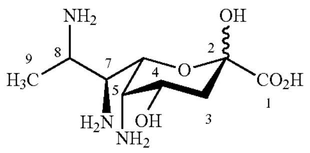

5,7,8-triamino-3,5,7,8,9-pentadeoxynon-2-ulosonic acid (unknown configuration at C-8) can be found in *Tenacibaculum maritimum* (former *Flexibacter maritimus*).

Accordingly, for the compounds of formulae Ia-1 to Ia-4, said bacteria are preferably selected among *Legionella pneumophila, Vibrio alginolyticus, Acinetobacter baumannii, Pseudomonas fluorescens, Vibrio salmonicida, Shewanella japonica, Pseudomonas aeruginosa* and *Tenacibaculum maritimum.*

More preferably, the said modified monosaccharide compound of the present invention is a compound having one the following formula (Ia-1), (Ia-1'), (Ib-1) or a salt thereof:

(Ia-1)

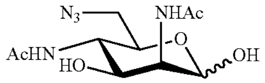

(Ia-1')

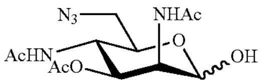

(Ib-1)

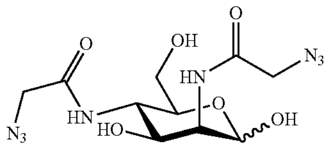

In a preferred embodiment, the method enables labeling living *Legionella pneumophila* bacteria with said compound of formula Ia-1 or Ib-1.

In practice, the samples taken from water containing environment media wherein *Legionella pneumophila* can be found such as water from air conditioning installation or device especially cooling towers or other water containing installation such as swimming pools, don't comprise other bacteria comprising the said endogenous residue of formula (Ic-1) or (Ic-2) so that if a labeling is detected, the method can be considered as labeling specifically *Legionella pneumophila.*

*Legionella pneumophila* is a pathogenic bacterium involved in regular outbreaks characterized by a relatively high fatality rate and an important societal impact. Regular monitoring of the presence of this bacterium in environmental water samples is necessary to prevent these epidemic events, but the traditional culture-based detection and identification method requires up to 10 days. The present invention provides a method allowing a quicker specific identification of *Legionella pneumophila* while other *Legionella* species and other genus are not labeled.

This compound Ia-1 (6-azido-2,4-diacetamido-2,4,6-trideoxy-D-mannopyranose) can penetrate most of the serogroups of *Legionella pneumophilia* and be metabolized in either Leg-$N_3$ and/or 4eLeg-$N_3$ and incorporated within the outer membrane in a said endogenous monosaccharide residue of said LPS layer of the outer membrane of the bacteria which can be a 4eLeg (4-epilegionaminic acid or 5,7-diamino-3,5,7,9-tetradeoxy-D-glycero-D-talo-non-2-ulosonic acid) or 4-epilegionaminate residue, or a leg (legionaminic acid=(5,7-diamino-3,5,7,9-tetradeoxy-D-glycero-D-galacto-non-2-ulosonic acid) or legionaminate residue, these two endogenous monosaccharides 4eLeg and Leg being present in most of the various different serogroups of *Legionella pneumophila* species interalia as it has been shown with the various different serogroups of *Legionella pneumophila* which have been tested.

More particularly, said modified monosaccharide compound is a compound having the following formula (Iy-1), or a salt thereof wherein:

Iy-1

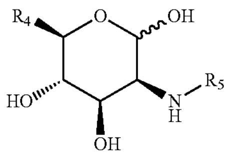

Wherein

R4 is H or an alkyl chain in $C_1$ to $C_4$, each carbon being substituted or not by OH or $NH_2$ substituted or not by protecting groups thereof, preferably by alkyl, hydroxyalkyl, acyl, formyl or imidoyl groups, preferably R4 being $CH_2OH$, and R5 can be alkyl, hydroxyalkyl, acyl, formyl or imidoyl groups, substituted or not, preferably R5 being $COCH_3$, and at least one of R4 and R5 groups being substituted by a said first reactive group.

The monosaccharide part of compounds of formulae (Iy-1) is precursor of the following nonulosonic acid type endogenous monosaccharide of formulae Ic-6, namely:

(Ic-6)=

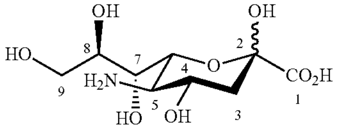

Neu (5-amino-3,5-dideoxy-D-glycero-D-galacto-non-2-ulosonic acid), (Ic-6) can be found in the CPS of *E. coli, Neisseria meningitidis, Moraxella nonliquefaciens*, and *Mannheimia* (*Pasteurella*) *haemolytica, Streptococcus agalactiae* (Gram +), *Streptococcus suis* (Gram +) and in the LPS O-antigen of bacteria including *Hafnia alvei, Escherichia albertii, Salmonella enterica, E. coli Citro-bacter, Vibrio cholerae, Shewanella algae*, and in the LPS core of several pathogens including *N. meningitidis, Neisseria gonorrhoeae, H. influenzae, Haemophilus ducreyi, Histophilus somni, Campylobacter jejuni*, and *Helicobacter pylori.*

In another particular embodiment, the method enables labeling specifically living *Pseudomonas aeruginosa* bacteria and said endogenous monosaccharide residue of said LPS layer of the outer membrane of the bacteria are:

either a 8-epilegionaminic acid (5,7-diamino-3,5,7,9-tetradeoxy-L-glycero-D-galacto-non-2-ulosonic acid) or 8-epilegionaminate residue, the said modified monosaccharide compound being a compound of formula (Ia-2)

or a pseudaminic acid (5,7-diamino-3,5,7,9-tetradeoxy-L-glycero-L-manno-non-2-ulosonic acid) or pseudaminate residue, and the said modified monosaccharide compound being a compound of formula (Ia-3).

Living bacteria comprise bacteria capable of multiplying as well as viable bacteria not capable to multiply. As most of the sanitary regulations refer to the numbering of bacteria capable to multiply, especially capable to multiply on a solid growth medium, advantageously, the present invention provides more particularly a method for labeling specifically bacteria capable of multiplying wherein said bacteria are incubated in a culture medium in (liquid medium) or on (solid medium) which said bacteria are capable to multiply.

Severe pathogens are hiding amongst Gram negative bacteria, and the rapid identification of viable cells represents a major sanitary challenge. The modified monosaccharides of the present invention are rapidly assimilated by the bacteria and enable fast labeling and detection thereof—the overall process taking less than one day, of metabolically active/viable wild type Gram negative bacteria. This method is very rapid in comparison to usual detection of viable bacteria which needs normally between 2 days and more than one month depending on the bacterial strain.

Advantageously, the present invention comprises the further step (c) of detecting living bacteria in detecting whether said bacteria comprise said labeling molecule bound to the glycans of their outer membrane and/or immobilizing said living bacteria bearing said labeling molecule onto a solid substrate, wherein said labeling molecule is a molecule comprising a detectable substance or capable to react or to be bound to a detectable substance or said labeling molecule is a first molecule bearing a said second reactive group, said first molecule being capable to react or to be bound to a second molecule and/or to a solid substrate, preferably said second molecule comprising a detectable substance and/or said second molecule being bound or capable to be bound to a said solid substrate.

Accordingly, the present invention enables (a) numbering or identification of detected living bacteria as well a (b) concentrating and/or isolating living bacteria immobilized on a solid support; especially with a solid support constituted of magnetic beads bearing the said second reactive group.

More particularly, the method enables specifically detecting living bacteria of a given category of bacteria in a sample comprising bacteria, wherein said labeling molecule is a detectable molecule comprising a detectable substance, the method comprising the step c) of detecting living bacteria in detecting whether said bacteria comprise said detectable molecule bound to the glycans of their outer membrane.

The said detecting step c) can be carried out in a liquid medium or on a solid substrate.

A more particularly, detection can occur with a detectable substance detected by fluorescence.

More particularly, said labeling molecule is a first ligand or first binding protein bearing a said second reactive group and in step c) said living bacteria coupled to said first ligand or first binding protein is detected and/or immobilized by contacting said first ligand or first binding protein with a second ligand or second binding protein reacting or binding specifically to said first ligand or first binding protein.

More particularly, said labeling molecule is a first ligand, preferably biotin, bearing a said second reactive group, and in step c) said living bacteria coupled to said first ligand are detected by reaction of said bacteria with an antibody or another protein specific to said first ligand, said antibody bearing a detectable substance, preferably a fluorochrome or luminescent molecule or an enzyme.

More particularly, the said first reactive group is selected among groups consisting in or bearing the group azido and groups consisting in or bearing the group alkyne, the said first reactive group being preferably the group azido, and the said second reactive group is selected among groups consisting in or bearing respectively the groups alkyne and azido, the said second reactive group being preferably the group alkyne, and reacting the said azido reactive group with the said alkyne reactive group is carried out in performing an azide alkyne cycloaddition.

The present invention provides also a kit for carrying out the method of the present invention comprising:

- a said analog of a monosaccharide compound of formula (I) substituted by a said first reactive group, said compound of formula I being a modified precursor able to be converted into a modified endogenous ulosonic acid residue incorporated into a polysaccharide of the outer membrane of a bacteria, especially into the LPS or CPS of the outer membrane of such bacteria, and
- a said labeling molecule comprising a said second reactive group capable of reacting with said first reactive group, and
- if required, reactants for generating the reaction of said first reactive group of said analog residue incorporated within said polysaccharides of the outer membrane of said bacteria with said second reactive group of said labeling molecule, and
- preferably, a culture or incubation medium allowing the growth of a said given category of bacteria, preferably specific to the growth of said given category of bacteria.

Preferably, the said first reactive group Ra is selected among groups consisting in or bearing the group azido ($—N_3$) and groups consisting in or bearing the group alkyne (—C≡C—), and the said second reactive group Rb is selected among groups consisting in or bearing respectively the groups alkyne (—C≡C—) and azido ($—N_3$), and reacting the said azido reactive group with a said alkyne group (—C≡C—) is carried out in performing an azide alkyne cycloaddition.

An azide alkyne cycloaddition is a well-known so-called click chemistry reaction in the presence or not of a copper catalyst wherein the azide group reacts with the alkyne group to afford a triazole. More particularly, the reaction can be carried out in copper catalyzed conditions in the presence of a tris-triazolyl ligand, preferably TGTA. More particularly, the detectable molecule is a fluorochrome bearing a terminal alkyne group.

More particularly, the reaction can be carried out in the presence of a tris-triazole ligand such as TGTA (Tris((1-(β-D-glucopyranosyl)-1H-[1,2,3]-triazol-4-yl)methyl)amine) or TBTA (Tris-[(1-benzyl-1H-1,2,3-triazol-4-yl) methyl] amine) and an Alexa labeling molecule bearing a terminal alkyne group with a catalyst so as to perform an azide alkyne cycloaddition of the said fluorochrome and said analog compound of formula (I).

Other appropriate ligands frequently used are: tris(3-hydroxypropyltriazolylmethyl)amine (THPTA), 2-(4-((bis ((1-tert-butyl-1 H-1,2,3-triazol-4-yl)methyl)amino)methyl)-1H-1,2,3-triazol-1-yl)ethanesulfonic acid (BTTES), Tris ((1-((O-ethyl) carboxymethyl)-(1,2,3-triazol-4-yl)) methyl) amine, bathophenanthroline disulfonate, or Tris(2-benzimidazolylmethyl)amines (53).

Alternatively, azide alkyne cycloaddition can be performed in the absence of copper, if a strained alkyne is used, such as azadibenzocyclooctyne (ADIBO, DIBAC or DBCO) or tetramethyldibenzocyclooctyne (TMDIBO).

Other appropriate strained alkynes frequently used for copper-free reaction include: cyclooctyne (OCT), aryl-less cyclooctyne (ALO), monofluorocyclooctyne (MOFO), difluorocyclooctyne (DIFO), dibenzocyclooctyne (DIBO), di methoxyazacyclooctyne (DIMAC), biarylazacyclooctynone (BARAC), bicyclononyne (BCN), tetramethylthiepinium (TMTI, TMTH), difluorobenzocyclooctyne (DIFBO), oxa-dibenzocyclooctyne (ODIBO), carboxymethylmonobenzocyclooctyne (COMBO), or benzocyclononyne.

Other reactive groups and other reactions are possible such as: Staudinger Ligation (first reactive group=azide and second reactive group=phosphine), copper-free click-chemistry (first reactive group=azide and second reactive group=constrained alkyne (intracyclic alkyne)), carbonyl condensation (first reactive group=aldehyde or ketone and second reactive group=hydrazide or oxyamine), thiol-ene click chemistry (first reactive group=thiol and second reactive group=alkene), nitrile-oxide-ene click chemistry (first reactive group=nitrile oxide or aldehyde, oxime, or hydroxymoyl chloride or chlororoxime and second reactive group=alkene or alkyne), nitrile imine-ene click chemistry (first reactive group=nitrile imine or aldehyde, hydrazone, or hydrazonoyl chloride or chlorohydrazone and second reactive group=alkene or alkyne), inverse electron demand Diels-Alder ligation (first reactive group=alkene and second reactive group=tetrazine), isonitrile-tetrazine click chemistry (first reactive group=isonitrile and second reactive group=tetrazine), Suzuki-Miyaura coupling (first reactive group=aryl halide and second reactive group=aryl boronate), His-tag (first reactive group=oligo-histidine and second reactive group=nickel-complex or nickel ligand).

In the above-mentioned listing of groups involved in the reactions, the first reactive group and the second reactive group can be permuted. All the above mentioned chemical reactions result in a covalent link.

Other and higher specificity of detection can be obtained in incubating the bacteria sample with two said different monosaccharide analog compounds and two different detectable molecules.

In another particular embodiment of the method of the present invention, the said incubation of step a) and reaction of step b) are carried out on a membrane filter so that the cultivated bacteria emanating from a same original bacterium which has been multiplied are grouped together and can be visualized with a microscope and the said detectable molecule can be detected by visualization with a said microscope. Therefore, the number of cultivable bacteria can be quantified thereby.

This embodiment enables to filter the tested sample on said membrane filter such as a polyester membrane, prior to assimilation of the said modified monosaccharide to avoid over-estimation of viable bacteria due to possible growth during the assimilation period. Indeed, when cells fixed on the top of such membrane start to grow, they stay together and form a micro-colony that can be easily detected as coming from the same single cell. Therefore, this enables to number by counting the cultivable bacteria.

The present invention also provides a kit for carrying out the method of the invention further comprising a culture or incubation medium allowing the growth of a said given category of bacteria, preferably specific to the growth of said given category of bacteria.

Preferably, the said culture or incubation medium further comprises agents enhancing and/or accelerating the growth speed and/or the capacity to form colonies of the said given category of bacteria. More particularly, the incubation medium comprises at least an antioxidant agent such as pyruvate or catalase.

To label specifically the Gram negative bacteria, it can be more advantageous to use a culture medium specific to Gram negative bacteria in steps a) and b) therefore not allowing culture of Gram positive bacteria.

More particularly, in one embodiment, the kit further comprises:

a said detectable molecule or said second molecule bearing a detectable substance, preferably a fluorochrome or luminescent molecule or an enzyme, and/or a solid substrate bearing a said second molecule capable of specifically reacting or binding with said labeling molecule.

More particularly, in one embodiment, the kit of the present invention further comprises:

a said detectable molecule comprising a said second reactive group capable of reacting with said first reactive group, and a solid medium allowing visualization of the bacteria after incubating with the said analog of a monosaccharide compound, said reactants and said detectable molecule.

More particularly again, the kit comprises:

a said modified monosaccharide compound substituted by a said first reactive group comprising an azido or alkyne group, and a said second reactive group of the detectable molecule bearing an alkyne or, respectively, azido group, and possibly, said reactants comprising a copper catalyst and a tristriazolyl ligand.

In a first particular embodiment, said labeling molecule can be a detectable molecule, namely a molecule consisting in or bearing a detectable substance, namely a substance capable to be detected such as a fluorochrome or luminescent substance or an enzyme such as peroxidase, said enzyme being more particularly detected after reacting with a co-reactant.

In a further particular embodiment, useful for isolating and/or concentrating living bacteria, the said labeling molecule can be bound to a solid substrate when carrying out step b).

In a further particular embodiment, said labeling molecule is a molecule which is a first ligand or first binding protein bearing a said second reactive group and in step c) said living bacteria coupled to said first ligand or first binding protein is detected and/or immobilized by contacting said first ligand or first binding protein with a second molecule which is a second ligand or second binding protein reacting or binding specifically to said first ligand or first binding protein.

Then, advantageously, said first or second ligand or binding protein can react or be bound to a third binding protein bearing a said detectable substance such as a fluorochrome or luminescent substance or an enzyme such as peroxidase, said third binding protein binding specifically to a said first and/or second ligand or binding protein. Detecting said detectable substance via a said second ligand or second binding protein or third binding protein enables to amplify the signal of the said detectable substance.

More particularly, the first ligand or first binding protein can be:

biotin, said second binding protein being then avidin or streptavidin and said third binding protein being an antibody raised against biotin, or avidin or streptavidin, said second ligand binding protein being then biotin and said third binding protein being an antibody raised against avidin or streptavidin, or a first antibody, said second binding protein being then a second antibody specific to said first antibody and said third binding protein being a third antibody specific to said first antibody.

More particularly, said labeling molecule is a first ligand, preferably biotin, bearing a said second reactive group, and in step c) said living bacteria coupled to said first ligand are detected by reaction of said bacteria with an antibody specific to said first ligand, said antibody bearing a detectable substance, preferably a fluorochrome or luminescent molecule or an enzyme.

More particularly again, said labeling molecule is a first ligand, preferably biotin, bearing a said second reactive group, and in step c) said living bacteria coupled to said first binding protein is immobilized by reacting said first ligand with a solid substrate, preferably magnetic beads, coupled to a said second binding protein, preferably avidin or streptavidin, before detecting said living bacteria by bacterial DNA enzymatic amplification or by reaction of said bacteria with a third binding protein reacting or binding specifically to said first ligand or second binding protein, said third binding protein bearing a detectable substance, preferably a fluorochrome or luminescent molecule or an enzyme, said third binding protein being preferably an antibody specific to said first ligand or first binding protein.

Such embodiment wherein said living bacteria are immobilized on said solid substrate enables to concentrate the sample into said bacteria and to quantify said living bacteria by any known method including DNA enzymatic amplification such as PCR, especially Real Time PCR or a method involving immunological reaction with a labeled antibody such as an ELISA test.

Other characteristics and advantages of the present invention will be more apparent in the light of the following detailed description and examples of illustrative and non-limitative embodiments referring to the following figures wherein:

FIG. 1: represents the Leg (compound Ib-1) pathway in *L. pneumophila;*

FIG. 2 represents the successive reactions of the synthesis of compounds Ia-1 and Ia-1';

FIGS. 3 to 7 represents detections of metabolically incorporated compound Ia-1 or Ia-1' by various bacteria strains as shown by CuI-catalyzed click reaction with the biotine-alkyne 5, and further visualization using an Alexa Fluor 488-IgG anti-biotin antibody. Phase contrast and fluorescence images in the presence of Ia-1 or Ia-1' (right panel) or absence of Ia-1 or Ia-1' (left panel), Scale bar=1 μm;

Figure 6:
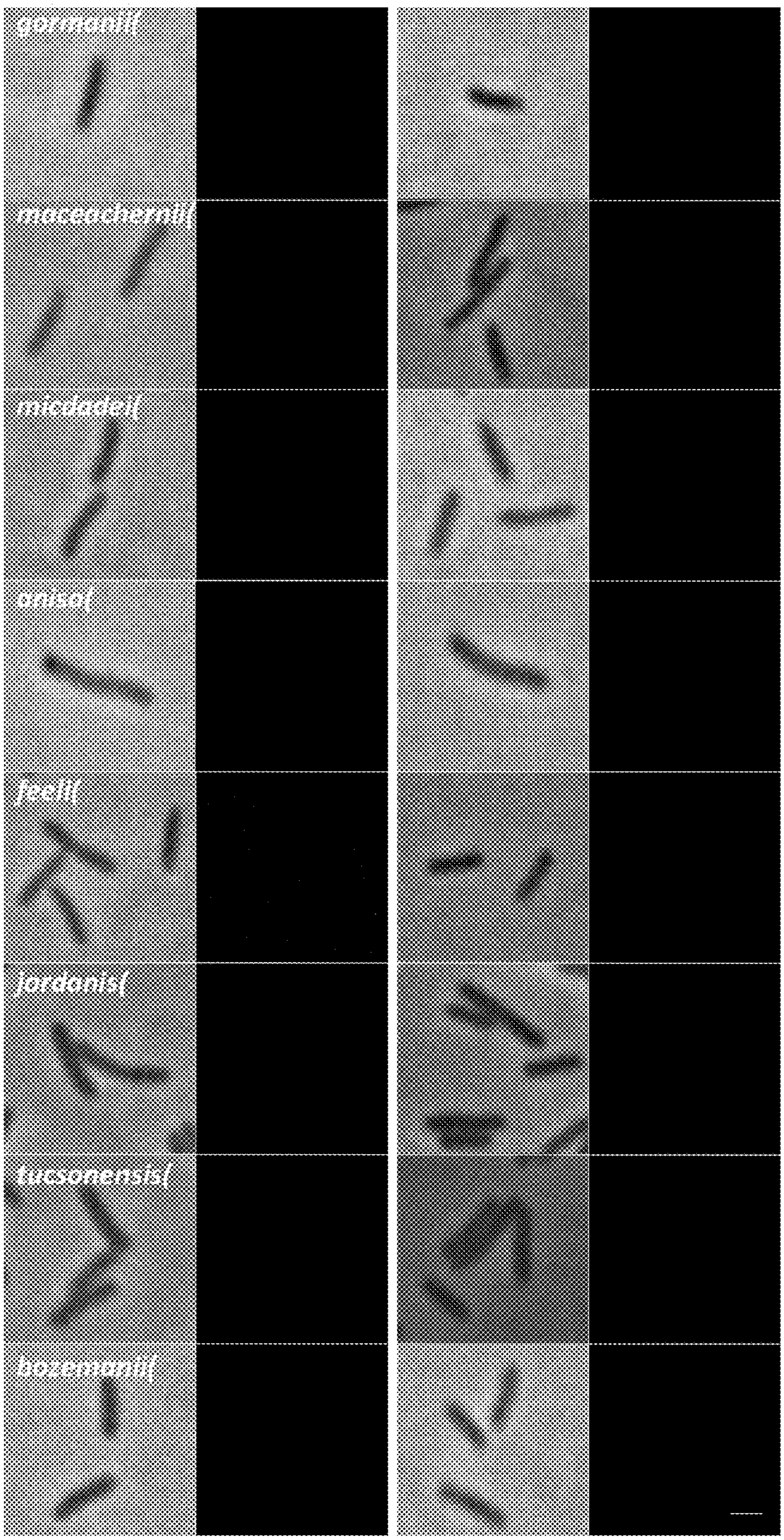
Figure 7:
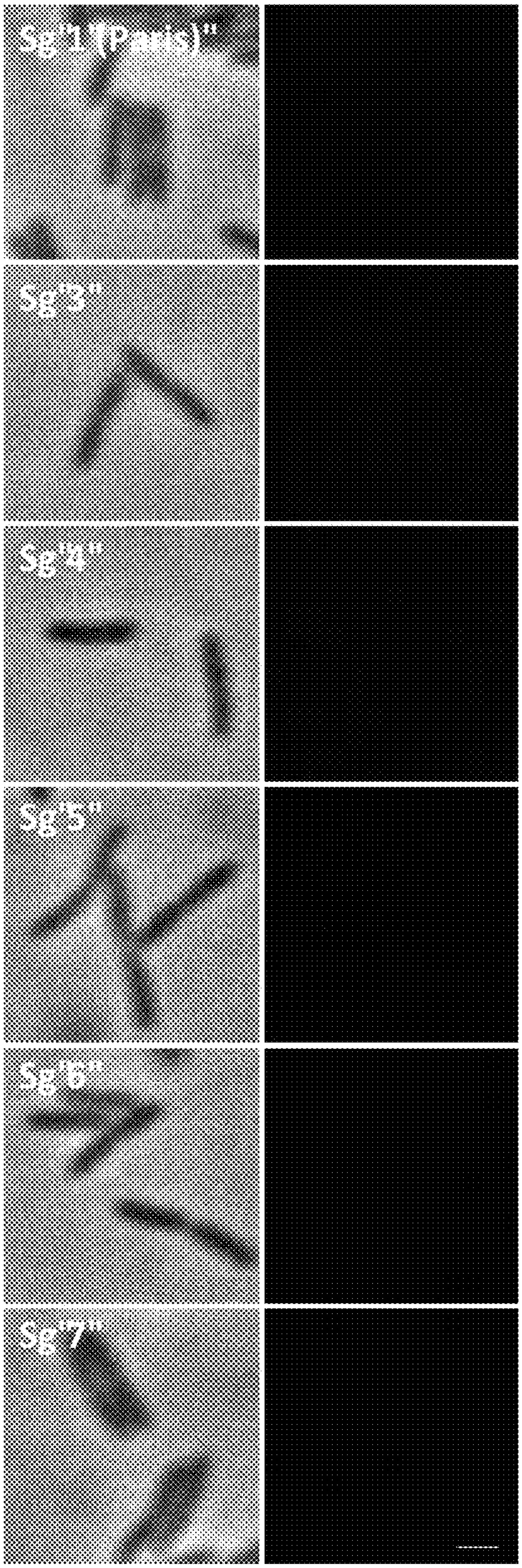

FIG. 6 represents photography of detection of metabolically incorporated compound Ia-1 by various *Legionella* strains (Compound Ia-1 is not incorporated by *Legionella* that not belong to the *L. pneumophila* species) and FIG. 7 represents photography of detection of: Detection of metabolically incorporated compound Ia-1' (Ia-1'=Ia-1 wherein OH is AcO in position R3). Compound Ia-1' is not incorporated by *L. pneumophila* in these conditions.

Figure 1:
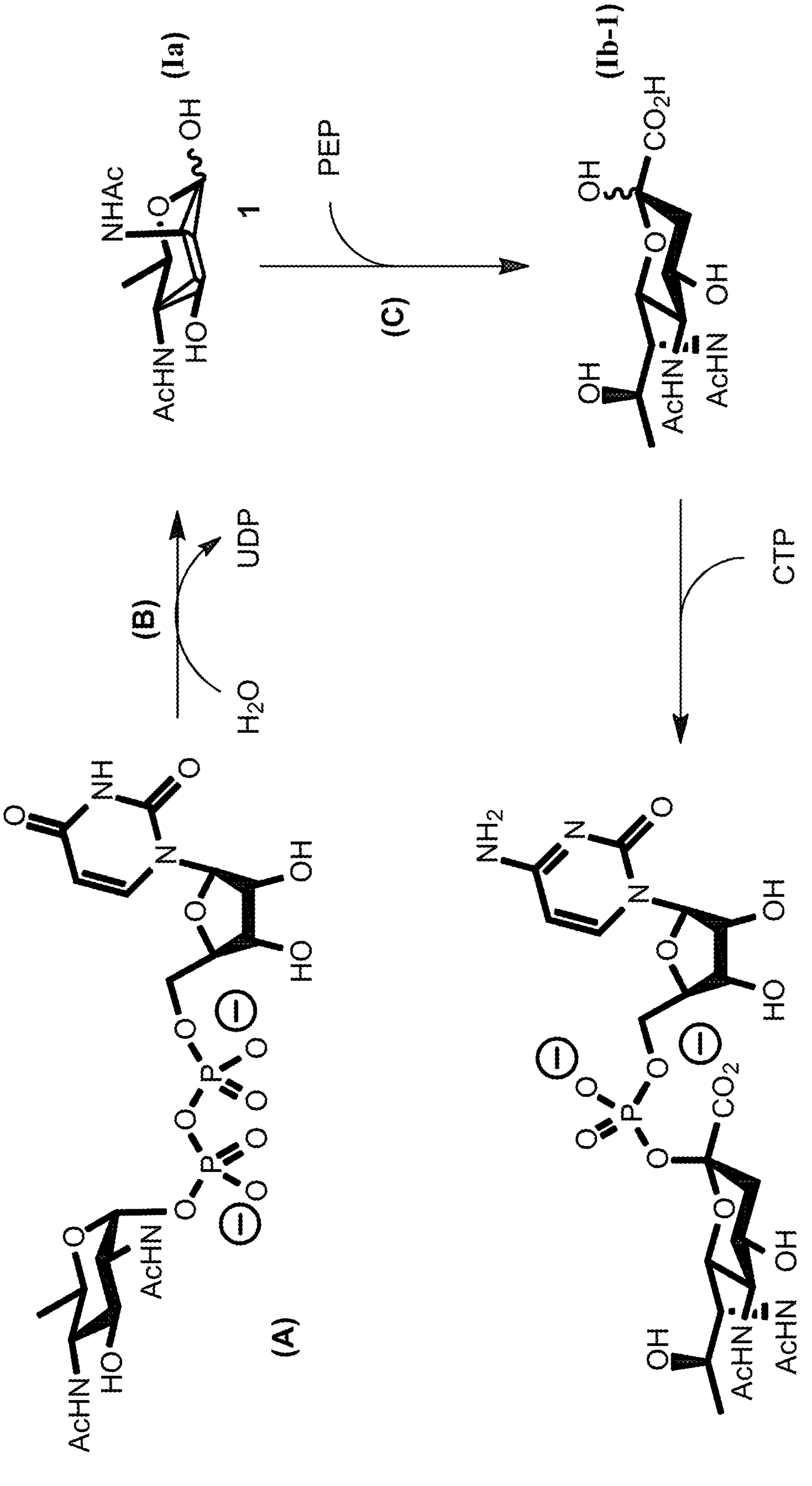

The O-antigen of *L. pneumophila* serogroup 1, which is prevalent among infected cases, has been shown [1] to be composed of an α-(2->4) homopolysaccharidic repeat of 5-N-acetimidoyl-7-N-acetyl-legionaminic acid (Leg5Am7Ac), with 8-O-acetylation in the Pontiac subgroup [2]. The biosynthesis of Leg (FIG. 1) starts from UDP-N,N'-diacetylbacillosamine (A), which is transformed into 2,4-diacetamido-2,4,6-trideoxy-D-mannopyranose (Ia) by the dual action of a hydrolysing 2-epimerase (B). In the next step, the free precursor Ia is directly transformed into Ib-1=N, N'-diacetyllegionaminic acid (Leg5Ac7Ac) Ib-1 via the action of an aldolase (C), in the presence of phosphoenolpyruvate (PEP)[3]. This event controls the stereochemistry of the newly generated stereogenic centre at C-4. Legionaminic acid is then activated in the form of a cytidine monophosphate donor (CMP)-Leg5Ac7Ac. Further transformations are believed to occur at a later stage.

In order to target the Leg pathway for metabolic glycan labeling, the synthesis of Ia-1 an azido derivative of Ia, namely 6-azido-2,4-diacetamido-2,4,6-trideoxy-D-mannopyranose (Ia-1), has been carried out as well as its less polar, mono-acetylated derivative (Ia-1'), which might enter more easily into the human cell via passive transport or within amibes or in biological sample comprising eukaryotic cells such as human samples, and be further transformed in Ia-1 by the action of intra-cellular, nonspecific esterases. A synthetic strategy starting from D-galactose has been developed, and the final products have been isolated and tested for their capacity to specifically label the LPS of living *L. pneumophila* serogroup 1.

Compounds Ia-1 and Ia-1' were synthesized (FIG. 2) using a method inspired from the approach described by Tsvetkov and coll. [7] for the synthesis of 1. Target compound, 6-azido-2,4-diacetamido-2,4,6-trideoxy-D-mannose Ia-1, was prepared in eleven steps from commercial β-D-galactose pentaacetate with an overall yield of 17%, while 3-O-acetyl-6-azido-2,4-diacetamido-2,4,6-trideoxy-D-mannose Ia-1' was obtained from the same starting material in twelve steps and 15% overall yield.

Figure 2:
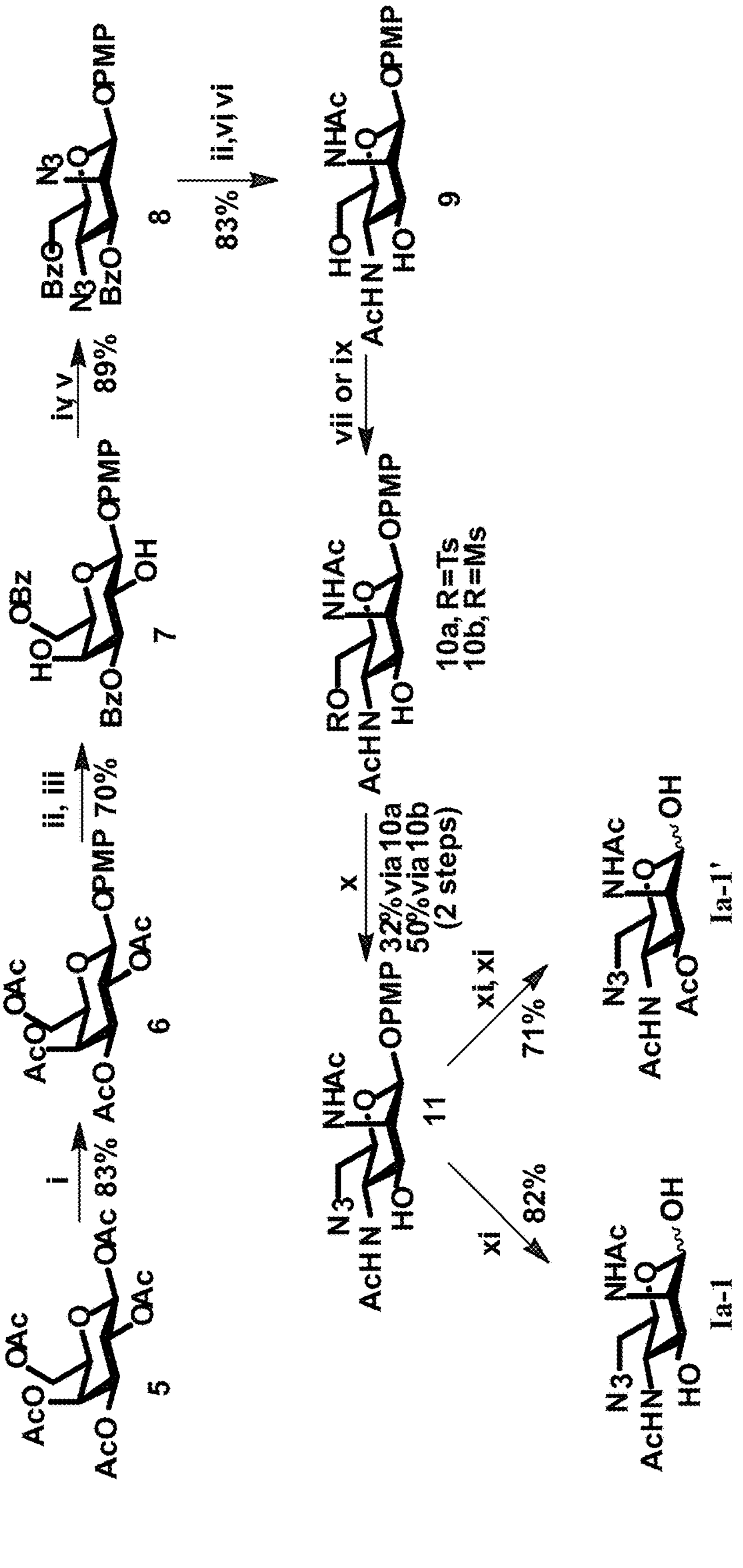

In the synthesis of FIG. 2 the following reagents and conditions have been used: (i) para-methoxyphenol, $BF_3.Et_2O$, $CH_2Cl_2$; (ii) $CH_3ONa$, $CH_3OH$; (iii) 2-aminoethyl diphenylborinate, DIPEA, benzoyl chloride, $CH_3CN$; (iv) $Tf_2O$, pyridine, $CH_2Cl_2$; (v) $Bu_4NN_3$, toluene; (vi) $Pd(OH)_2/C$, $H_2$, $CH_3OH$, ii) $Ac_2O$, $CH_3OH$; (viii) tosyl chloride, pyridine; (ix) mesyl chloride, pyridine; (x) $NaN_3$, DMF; (xi) CAN, $CH_3CN/H_2O$ (3:1); (xii) $Ac_2O$, pyridine, $CH_2Cl_2$ Glycosylation of β-D-galactose pentaacetate with p-methoxyphenol in the presence of boron trifluoride etherate gave 6 in a good 83% yield [4]. Zemplén deacetylation using sodium methoxide [5] followed by selective benzoylation using the method developed by Taylor, in the presence of 2-aminoethyl diphenylborinate as a catalyst led to 7 (70% yield over 2 steps) [6]. Conversion of 7 into the bis-triflate derivative, and its subsequent reaction with tetrabutylammonium azide in toluene resulted into the bis-azido compound 8 (89% over 2 steps), [7] the manno configuration of which was confirmed by 1H NMR ($J_{1,2}$=1.2 Hz; $J_{2,3}$=3.6 Hz; $J_{3,4}$=10.0 Hz; $J_{4,5}$=10.2 Hz). Conventional debenzoylation of 8 using sodium methoxide and reduction of the azido groups with dihydrogen in the presence of $Pd(OH)_2/C$ was followed by N-acetylation to give 9 in a high yield (82% over 3 steps) [7]. The azido derivative 11 was obtained in 2 steps by selective tosylation or mesylation in pyridine, followed by nucleophilic substitution using sodium azide in dimethylformamide [8].

In this strategy, mesylation followed by the substitution gave better result (50%) than the tosylation route (32%). Final product Ia-1 was obtained in a good yield (82%) from 11 by deprotection of the anomeric position using cerium ammonium nitrate in an acetonitrile/water mixture [9]. Alternatively, product Ia-1' was prepared in 2 steps from 11 in a respectable 71% yield, by acetylation followed by deprotection of the anomeric position using the same conditions as before [9].

EXAMPLE 1: SYNTHESIS OF COMPOUNDS IA-1, IA-1' AND IB-1

1) Materials for the Synthesis

Thin layer chromatography was performed over Merck 60 F254 with detection by UV, and/or by charring with sulphuric acid or $KMnO_4$ or phosphomolybdic acid solutions. Silica gel 60 40-63 μm was used for flash column chromatography.

NMR spectra were taken on Bruker Avance 300 or 500 MHz spectrometers, using the residual protonated solvent as internal standard. Chemical shifts δ are given in parts per million (ppm) and coupling constants are reported as Hertz (Hz). Splitting patterns are designated as singlet (s), doublet (d), triplet (t), doublet of doublet (dd), doublet of doublet of doublet (ddd). Splitting patterns that could not be interpreted or easily visualized are designated as multiplet (m).

Mass spectra were taken on a Thermo Scientific TSQ or on a Bruker micrOTOFq or on a Waters LCT Premier XE (ToF), with electrospray ionization in the positive (ESI+) mode of detection.

IR-FT spectra were recorded on a Perkin Elmer Spectrum 100 spectrometer. Characteristic absorptions are reported in $cm^{-1}$.

Specific optical rotations were measured at 20° C. with an Anton Paar MCP 300 polarimeter in a 10-cm cell at 20° C. and 589 nm.

Melting points were measured with a Bŭchi Melting Point B-540 instrument.

2) Method of the Synthesis of Compounds Ia-1 and Ia-1'

2.1) Preparation of 4-Methoxyphenyl 2,3,4,6-tetra-O-acetyl-β-D-galactopyranoside (6) (First Step FIG. 2) of the Following Formula (6)

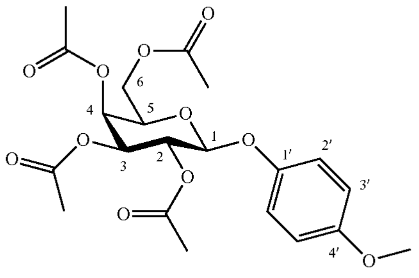

To a solution of β-D-galactose pentaacetate 5 (25.00 g, 64.0 mmol) and p-methoxyphenol (9.54 g, 76.9 mmol) in $CH_2Cl_2$ (500 mL), $BF_3.Et_2O$ (9.73 mL, 76.9 mmol) was added at 0° C. The reaction was allowed to warm to room temperature, stirred for 15 hours and then quenched with HCl (1 mol·L-1, 250 mL). The organic layer was washed with saturated aq. $NaHCO_3$ (2×250 mL) and brine (150 mL) then dried with anhydrous $Na_2SO_4$, filtrated and concentrated to give pale yellow oil. The residue was recrystallized from $CH_3OH$ to afford compound 6 (24.1 g, 83%) as white crystals.

2.2) Preparation of 4-Methoxyphenyl β-D-galactopyranoside (6') of the Following Formula (6')

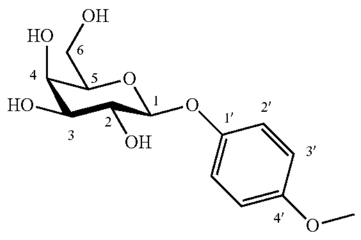

A freshly prepared solution of sodium methoxide (0.2 mol·$L^{-1}$, 4.4 mL) was added to a stirred solution of compound 6 (4.0 g, 8.80 mmol) in $CH_3OH$ (44 mL). The mixture was stirred for 40 min at room temperature and then Amberlite IRN-77 resin (H+ form) was added to neutralize the solution. Filtration and evaporation of the solvent from the filtrate afforded a white amorphous solid (6', 2.52 g) which was not further purified. A small portion was recrystallized from ethanol to obtain white needles which were used for the characterization of the compound.

2.3) Preparation of 4-Methoxyphenyl 3,6-di-O-benzoyl-β-D-galactopyranoside (7) (Second Step in FIG. 2 of the Following Formula (7)

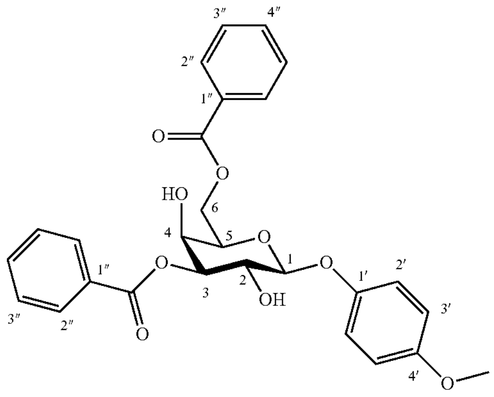

2-Aminoethyl diphenylborinate (79 mg, 0.35 mmol) and compound 6' (1.00 g, 3.49 mmol) were placed in a 50 mL round bottom flask, dried under vacuum for 30 min, then dissolved in dry $CH_3CN$ (17.5 mL). N,N-Diisopropylethylamine (2.43 mL, 13.96 mmol) and benzoyl chloride (1.62 mL, 13.96 mmol) were added and the resulting mixture was stirred at room temperature for 1 hour. The mixture was then diluted with ethyl acetate (30 mL), washed with $H_2O$ (30 mL), and extracted three times with ethyl acetate (30 mL).

The combined organic layers were dried over anhydrous $Na_2SO_4$, filtered, and concentrated under reduced pressure. The resulting crude material was purified by flash column chromatography on silica gel ($CH_2Cl_2$/ethyl acetate 92:8) to afford compound 7 (1.21 g, 70%) as a white powder.

2.4) Preparation of 4-Methoxyphenyl 2,4-diazido-2,4-dideoxy-3,6-di-O-benzoyl-β-D-mannopyranoside (8) (Third Step in FIG. 2) of the Following Formula (8)

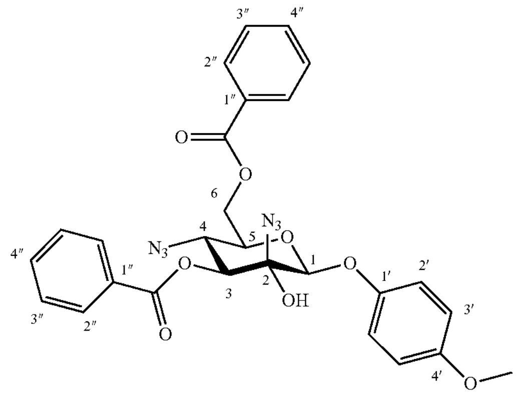

Trifluoromethanesulfonic anhydride (2.02 mL, 12.0 mmol) was added dropwise at 0° C. to a solution of compound 7 (1.98 g, 4.0 mmol) and dry pyridine (1.94 mL, 24.0 mmol) in $CH_2Cl_2$ (27.0 mL). The mixture was stirred at 0° C. for 1 h30, diluted with $CHCl_3$ (60 mL), and washed successively with $H_2O$ (50 mL), a solution of 1N aq. HCl (50 mL), $H_2O$ (50 mL), a saturated aqueous solution of $CuSO_4$, and a saturated solution of NaCl, and then concentrated under vacuum. The crude bis-triflate (Rf=0.48, cyclohexane/ethyl acetate 7:3) obtained was dissolved in toluene (27.0 mL) and tetra-n-butylammonium azide (6.83 g, 24.0 mmol) was added. After stirring 1 h30 at 65-70° C. and 1 h30 at 100° C., the mixture was cooled, diluted with toluene (60 mL), washed twice with water (50 mL), a saturated solution of NaCl, and concentrated. Flash column chromatography on silica gel of the residue (cyclohexane/ethyl acetate 8:2) afforded compound 8 (1.95 g, 89%) as a white foam.

2.5) Preparation of 4-Methoxyphenyl 2,4-diazido-2,4-dideoxy-β-D-mannopyranoside (8') of the Following Formula (8')

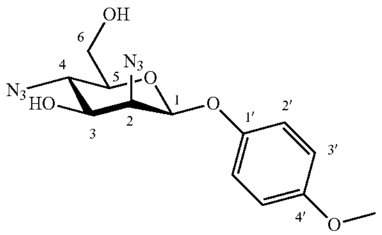

A solution of sodium methoxide in $CH_3OH$ (2 mol·$L^{-1}$, 0.22 mL, 0.44 mmol) was added to a solution of compound 8 (630 mg, 1.15 mmol) in dry $CH_3OH$ (4.6 mL) and the mixture was stirred for 1 hour at room temperature. The reaction mixture was then neutralized by adding Amberlite IRN-77 (H+ form) ion-exchange resin. Filtration and evaporation of the filtrate afforded crude compound 8' (380 mg) as a white solid which was used for the next step without further purification. An analytical sample was purified by flash column chromatography on silica gel (cyclohexane/ethyl acetate 9:1 to 6:4) for characterisation.

2.6) Preparation of 4-Methoxyphenyl 2,4-diacetamido-2,4-dideoxy-β-D-mannopyranoside (9) of the Following Formula (9)

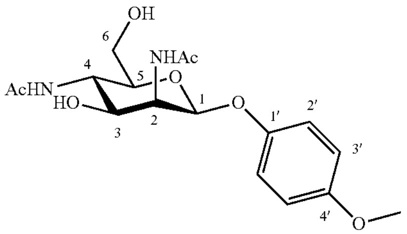

A solution of crude compound 8' (380 mg, 1.13 mmol) in $CH_3OH$ (8.5 mL) was hydrogenated with 20% $Pd(OH)_2/C$ (101 mg) at 30° C. for 1.5 hours. The catalyst was filtered off through Celite® and the filtrate was concentrated to dryness. The crude residue was dissolved in $CH_3OH$ (5 mL), acetic anhydride (0.43 mL, 4.52 mmol) was added and the mixture was stirred for 1 hour at room temperature. The residue obtained after evaporation of the solvent, was purified by flash column chromatography on silica gel ($CH_2Cl_2$/$CH_3OH$, 92:8) to afford compound 9 (342 mg, 82%) as a white solid.

2.7) Preparation of 4-Methoxyphenyl 2,4-diacetamido-2,4-dideoxy-6-O-tosyl-β-D-mannopyranoside (10a) of the Following Formula (10a)

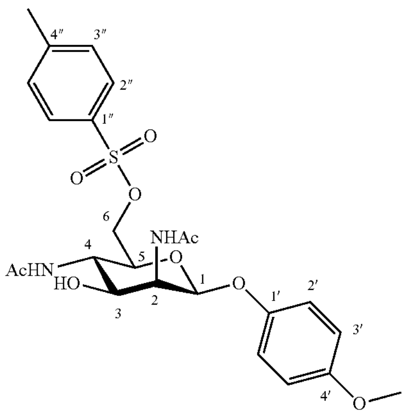

To a solution of compound 9 (100 mg, 0.27 mmol) in dry pyridine (0.6 mL) was added a solution of tosyl chloride (207 mg, 1.09 mmol) in dry pyridine (0.5 mL) at 0° C. and the mixture was stirred for 30 min. The reaction mixture was then quenched with $CH_3OH$ (1.0 mL) and solvent was evaporated under reduced pressure. Purification of the solid residue by flash column chromatography on silica gel ($CH_2Cl_2/CH_3OH$ 92:8) afforded compound 10a (90 mg, 64%) as a white powder.

2.8) Preparation of 4-Methoxyphenyl 2,4-diacetamido-2,4-dideoxy-6-O-mesyl-β-D-mannopyranoside (10b) of the Following Formula (10b)

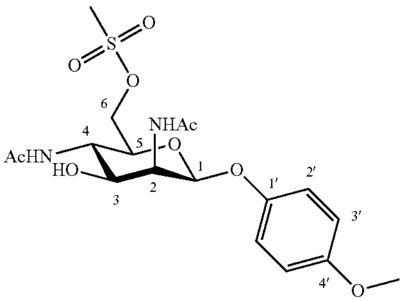

To a solution of compound 9 (460 mg, 1.25 mmol) in dry pyridine (5.1 mL) at −10° C. was added mesyl chloride (0.145 mL, 1.88 mmol) and the mixture was stirred at −10° C. for 45 min. The reaction was then quenched with $CH_3OH$ and the solvent evaporated under vacuum. The crude residue was purified by flash column chromatography on silica gel ($CH_2Cl_2/CH_3OH$ 92:8) to yield compound 10b (411 mg, 74%) as a white solid.

2.9) Preparation of 4-Methoxyphenyl 6-azido-2,4-diacetamido-2,4,6-trideoxy-β-D-mannopyranoside (11) of the Following Formula (11)

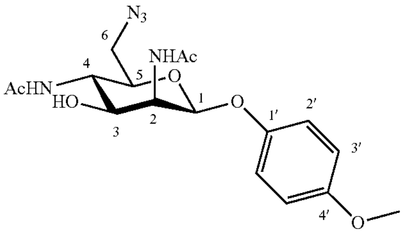

2.9.1) Starting from Tosylate (10a)

Tosylate 10a (43 mg, 0.08 mmol) and $NaN_3$ (16 mg, 0.25 mmol) were dissolved in dry dimethylformamide (0.80 mL) and the reaction mixture was stirred for 15 hours at 80° C. Then the reaction mixture was cooled to room temperature and concentrated. The crude solid was purified by flash column chromatography on silica gel ($CH_2Cl_2/CH_3OH$ 92:8) to give compound 11 (16 mg, 50%).

2.9.2) Starting from Mesylate 10b

Mesylate 10b (100 mg, 0.22 mmol) and $NaN_3$ (44 mg, 0.67 mmol) were dissolved in dry dimethylformamide (2.2 mL) and the reaction mixture was stirred for 15 h at 80° C. Then the reaction mixture was cooled to room temperature and the solvent was evaporated under reduced pressure. The residue was purified by flash column chromatography on silica gel ($CH_2Cl_2/CH_3OH$ 92:8) to afford compound 11 (59 mg, 67%) as a white solid.

2.10) Preparation of the 4-Methoxyphenyl 3-O-acetyl-6-azido-2,4-diacetamido-2,4,6-trideoxy-β-D-mannopyranoside (11') of the Following Formula

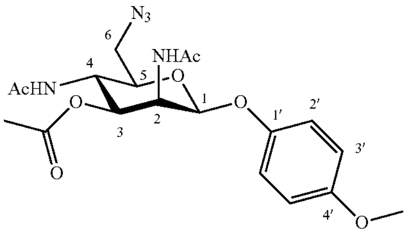

Dry pyridine (0.015 mL, 0.18 mmol) and acetic anhydride (0.008 mL, 0.09 mmol) were added to a stirred solution of compound 11 (12 mg, 0.03 mmol) in dry $CH_2Cl_2$ (0.25 mL) and the resulting mixture was stirred 3 hours at room temperature. More pyridine (0.008 mL, 0.09 mmol) and acetic anhydride (0.005 mL, 0.05 mmol) were added and the reaction mixture was stirred for 2 hours at room temperature. A saturated solution of $NH_4Cl$ was then added and aqueous layer was extracted with $CH_2Cl_2$. The combined organic extracts were washed with brine, dried over anhydrous $Na_2SO_4$, filtered and concentrated under reduced pressure. The crude residue was purified by flash column chromatography on silica gel ($CH_2Cl_2/CH_3OH$ 95:5) to yield compound 11' (12 mg, 90%) as a white solid.

2.11) Preparation of 3-O-Acetyl-6-azido-2,4-diacetamido-2,4,6-trideoxy-D-mannose (Ia-1') of the Following Formula

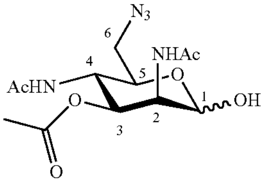

To a solution of compound 11' (20 mg, 0.046 mmol) in $CH_3CN/H_2O$ (0.8 mL, 3:1) was added cerium ammonium nitrate (75 mg, 0.138 mmol). The resulting clear orange solution was stirred at room temperature for 20 min and then loaded onto a silica gel column. Elution with $CH_2Cl_2/CH_3OH$ (94:6) gave compound 3 and a mixture of other compounds. Purification of the mixture by flash column chromatography on silica gel ($CH_2Cl_2/CH_3OH$ 94:6) yielded compound 3 (12 mg, 79%) as mixture of α/β anomers (17:83) as a white solid.

Rf ($CH_2Cl_2/CH_3OH$ 9:1): 0.46.

IR (cm-1): 3277, 2103, 1660, 1372, 1071.

1H-NMR (500 MHz, $CD_3OD$) δ: 5.27 (dd, 0.8H, J=10.7 and 4.3 Hz, H-3 β); 5.07 (d, 0.8H, J=1.4 Hz, H-1 β); 4.95 (d, 0.2H, J=1.4 Hz, H-1 α); 4.92 (dd, 0.2H, J=11.1 and 4.2 Hz, H-3 α); 4.57 (dd, 0.2H, J=4.2 and 1.4 Hz, H-2 α); 4.46 (dd, 0.8H, J=4.3 and 1.4 Hz, H-2 β); 4.13 (dd, 0.8H, J=10.7 and 10.5 Hz, H-4 β); 4.08 (ddd, 0.8H, J=10.5 and 7.3 and 1.9 Hz, H-5 β); 4.02 (dd, 0.2H, J=11 and 9.8 Hz, H-4 α); 3.55 (ddd, 0.2H, J=9.8 and 7.9 and 2.1 Hz, H-5 α); 3.51 (dd, 0.2H, J=12.6 and 7.9, H-6a α); 3.46 (dd, 0.8H, J=13.1 and 7.3 Hz, H-6a β); 3.32-3.3 (m, 0.2H, H-6b α); 3.28 (dd, 0.8H, J=13.1 and 1.9 Hz, H-6b β); 2.06, 2.05, 2.03, 2.02, 1.95, 1.93 (s, 9H, 3 CO—$CH_3$).

13C-NMR (75 MHz, $CD_3OD$) δ: 174.0, 173.9, 172.1 (3 C═O α and β); 94.7 (C-1 β); 94.5 (C-1 α); 76.4 (C-5 α); 73.4 (C-3 α); 71.9 (C-5 β); 70.8 (C-3 β); 53.3 (C-6 β); 53.2 (C-6 α); 52.6 (C-2 α); 52.0 (C-2 β); 48.5 (C-4 β), 47.7 (C-4 α); 22.8, 22.6 (2 CO—$CH_3$ (NHAc) α and β); 21.0 (CO—$CH_3$ α and β).

HMRS (ESI+): [M+H]+ ($C_{12}H_{20}N_5O_6$) Calc. m/z: 330.1408. found: 330.1391.

2.12) Preparation of 6-Azido-2,4-diacetamido-2,4,6-trideoxy-D-mannose (Ia-1) of the Following Formula

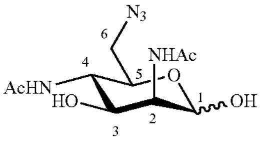

To a solution of compound 11 (90 mg, 0.23 mmol) in $CH_3CN/H_2O$ (3.6 mL, 3:1) was added cerium ammonium nitrate (376 mg, 0.69 mmol). The resulting clear orange solution was stirred at room temperature for 20 min and then loaded onto a silica gel column. Elution with $CH_2Cl_2/CH_3OH$ (88:12) gave compound 2 and a mixture of other compounds. Purification of the mixture by flash column chromatography on silica gel ($CH_2Cl_2/CH_3OH$ 88:12) yields compound 2 (54 mg, 82%) as mixture of α/β anomers (12:88) as a white solid.

Rf ($CH_2Cl_2/CH_3OH$ 88:12): 0.23.

IR (cm-1): 3302, 2988, 2107, 1646, 1552, 1376, 1075.

1H-NMR (500 MHz, $CD_3OD$) δ: 5.09 (d, 0.88H, J=1.2 Hz, H-1 β); 4.84 (d, 0.12H, J=0.9 Hz, H-1 α); 4.44 (dd, 0.12H, J=4.0 and 0.9 Hz, H-2 α); 4.26 (dd, 0.88H, J=4.5 and 1.2 Hz, H-2 β); 4.07 (dd, 0.88H, J=10.0 and 4.5 Hz, H-3 β); 3.96 (ddd, 0.88H, J=10.2 and 6.9 and 2.1 Hz, H-5 β); 3.93 (dd, 0.88H, J=10.2 and 10.0 Hz, H-4 β); 3.79 (dd, 0.12H, J=10.4 and 9.7 Hz, H-4 α); 3.73 (dd, 0.12H, J=10.4 and 4.0 Hz, H-3 α); 3.38 (dd, 0.12H, J=12.7 and 8.0, H-6a α); 3.44 (ddd, 0.12H, J=9.7 and 8.0 and 2.3 Hz, H-5 α); 3.40 (dd, 0.88H, J=13.2 and 6.9 Hz, H-6a β); 3.34-3.24 (m, 0.12H, H-6b α); 3.27 (dd, 0.88H, J=13.2 and 2.1 Hz, H-6b β); 2.08, 2.05, 2.00, 1.98 (s, 6H, 2 CO—$CH_3$).

13C-NMR (75 MHz, $CD_3OD$) δ: 174.5, 174.3 (2 C═O α and β); 95.1 (C-1 α); 94.6 (C-1 β); 76.6 (C-5 α); 72.0 (C-3 α); 71.9 (C-5 β); 68.3 (C-3 β); 55.5 (C-2 α); 54.9 (C-2 β); 53.5 (C-6 β); 53.4 (C-6 α); 51.3 (C-4 β), 51.3 (C-4 α); 23.0, 22.9, 22.7 (2 CO—$CH_3$ (NHAc) α and β).

HMRS (ESI+): [M+H]+ ($C_{10}H_{18}N_5O_5$) Calc. m/z: 288.1302. found: 288.1297.

3) Synthesis of 2,4-diazidoacetamido-2,4-dideoxy-D-mannose

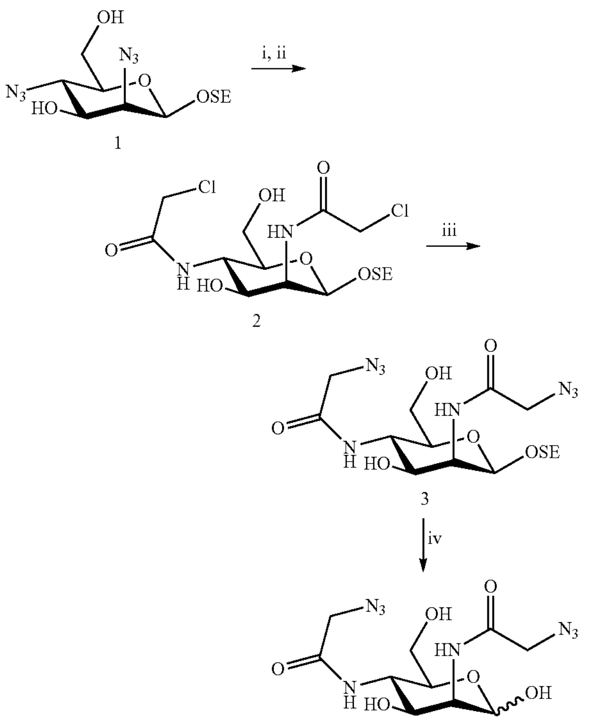

Conditions and reagents: i) $H_2$, $Pd(OH)_2/C$, $CH_3OH$, 30° C., 4 hours; ii) $(ClCH_2CO)_2O$, $Et_3N$, $CH_3OH$, r.t., 2 days; iii) $NaN_3$, DMF, 50° C., overnight; iv) TFA, $CH_2Cl_2$, 1 hour.

3.1) synthesis of 1-Trimethylsilylethanyl 2,4-dichloroacetamido-2,4-dideoxy-β-D-mannopyranoside (2)

A solution of compound 1 (80.0 mg, 0.24 mmol, 1.0 eq.) in $CH_3OH$ (1.8 mL, 0.13 M) was hydrogenated with 20% $Pd(OH)_2/C$ (23.4 mg) at 30° C. for 4 hours. The catalyst was filtered off through Celite® plug and the filtrate was concentrated under vaccum. The crude residue (70.8 mg, 0.25 mmol, 1.0 eq.) was dissolved in $CH_3OH$ (2.1 mL, 0.12 M), chloroacetic anhydride (299.3 mg, 1.75 mmol, 7.0 eq.) and $Et_3N$ (244 μL, 1.75 mmol, 3.0 eq.) were added. The mixture was stirred at room temperature for 2 days and then concentrated under reduced pressure. The residue was purified by flash chromatography over silica gel ($CH_2Cl_2/CH_3OH$ 100:0 to 80:20) to afford compound 2 (33.1 mg, 31%) as colourless oil.

3.2) 1'-Trimethylsilylethanyl2,4-diazidoacetamido-2,4-dideoxy-β-D-mannopyranoside (3)

To a solution of 2 (30.3 mg, 72.0 umol, 1.0 eq.) in dry DMF (0.5 mL, 0.14 M) wad added $NaN_3$ (54.5 mg, 1.24 mmol, 11.8 eq.). The reaction mixture was stirred at 50° C. overnight and then concentrated under reduced pressure. The crude residue was purified by flash chromatography over silica gel ($CH_2Cl_2$/acetone/$CH_3OH$ 90:6:4) to give compound 3 (26.8 mg, 86%) as a white foam.

3.3) 2,4-diazidoacetamido-2,4-dideoxy-D-mannose (4/Ib-1)

To a solution of 3 (20.6 mg, 46.0 umol, 1.0 eq.) in $CH_2Cl_2$ (460 μL, 0.10 M) was added slowly TFA (528 μL, 6.9 mmol, 150.0 eq.). The reaction mixture was stirred at room temperature for 1 hour and then co-evaporated three times with a mixture of toluene/EtOAc. The crude residue was purified by C-18 column chromatography ($H_2O$) and lyophilized to afford compound 4 (13.8 mg, 87%) as a mixture of α/β anomers (1:3) as white foam.

Rf ($CH_2Cl_2/CH_3OH$ 95:5): 0.28.

IR (cm-1): 3283, 2952, 2841, 2120, 1646, 1450, 1409, 1013.

HRMS (ESI+): [M+H]+ ($C_{10}H_{17}N_8O_6$) Calc. m/z 345.1271. found 345.1233.

Anomer alpha:

$^1$H-NMR (500 MHz, $CD_3OD$) δ: 5.10 (d, 1H, $J_{1,2}$ 1.7 Hz, H-1); 4.34 (dd, 1H, $J_{2,3}$ 4.4, $J_{2,1}$ 1.7 Hz, H-2); 4.17 (dd, 1H, $J_{3,4}$ 10.9, $J_{3,2}$ 4.4 Hz, H-3); 3.97 (d, 1H, $J_{2''a,2''b}$ 16.5 Hz, CH-2"a); 3.94 (d, 1H, $J_{2''a,2''b}$ 16.5 Hz, CH-2"b); 3.94 (d, 1H, $J_{2''c,2''d}$ 16.1 Hz, CH-2"c); 3.91 (d, 1H, $J_{2''c,2''d}$ 16.1 Hz, CH-2"d); 3.90-3.79 (m, 1H, H-5); 3.83 (dd, 1H, $J_{4,3}$ 10.9, $J_{4,5}$ 9.8 Hz, H-4); 3.70-3.60 (m, 2H, H-6).

13C-NMR (125 MHz, $CD_3OD$) δ: 171.4, 171.1 (2 C═O); 94.8 (C-1); 72.5 (C-5); 68.0 (C-3); 62.8 (C-6); 54.9 (C-2); 53.2, 52.8 ($CH_2$—$N_3$); 50.2 (C-4).

Anomer beta:

$^1$H-NMR (500 MHz, $CD_3OD$) δ: 4.88 (d, 1H, $J_{1,2}$ 1.6 Hz, H-1); 4.46 (dd, 1H, $J_{2,3}$ 3.9, $J_{2,1}$ 1.6 Hz, H-2); 3.99-3.79 (m, 4H, 2 CH-2"); 3.92-3.80 (m, 1H, H-4); 3.92-3.80 (m, 1H, H-3); 3.70-3.60 (m, 2H, H-6); 3.36 (ddd, 0.6H, $J_{5,4}$ 9.7, $J_{5,6}$ 4.0, $J_{5,6}$ 2.6 Hz, H-5).

13C-NMR (125 MHz, $CD_3OD$) δ: 171.4, 171.1 (2 C═O); 95.0 (C-1); 77.4 (C-5); 71.8 (C-3); 62.7 (C-6); 55.7 (C-2); 53.2, 52.8 ($CH_2$—$N_3$); 50.1 (C-4).

EXAMPLE 2: LABELING THE LPS OF LIVING *L. PNEUMOPHILA*

1) Material and Methods

1.1) Bacterial Strains and Growth Conditions

*Legionella* strains (Table 1) are grown in Yeast Extract medium supplemented with L-Cysteine, ferric pyrophosphate and α-ketoglutarate (YEC). *E. coli* K12 (MG1655) and *P. aeruginosa* (ATCC 9027) were grown in Luria-Bertani (LB) medium. All strains were grown in a rotary shaker (160 rpm) at 37° C. All strains were provided by the CNRL (Centre National de Référence sur *Legionella*).

TABLE 1

| *Legionella* species | Serogroup | Type |
|---|---|---|
| *Legionella pneumophila* | | |
| Philadelphia 2 | 1 | 33152 |
| Paris | 1 | CIP 33152 |
| Lens | 1 | CIP 108286 |
| | 1 | LG 0901 3003 |
| | 3 | LG 0903 1009 |
| | 4 | LG 0905 1005 |
| | 5 | LG 0905 3003 |
| | 6 | LG 0846 3022 |
| | 7 | LG 0824 4007 |

TABLE 1-continued

| *Legionella* species | Serogroup | Type |
|---|---|---|
| *Legionella* spp. | | |
| *L. gormanii* | | HL 0540 3034 |
| *L. maceachernii* | | HL 0540 G20 2029 |
| *L. micdadei* | | HL 0522 5034 |
| *L. bozemanii* | | HL 0538 2034 |
| *L. feelii* | | HL 0418 4001 |
| *L. jordanis* | | HL 0450 5001 |
| *L. tucsonensis* | | HL 0438 3117 |
| *L. anisa* | | CH47 ATCC 35291 |

1.2) Copper Catalyzed Click Chemistry

Overnight cultures were diluted 100 times in fresh medium (final volume 100 μl) containing 2 or 3 (4 mM). Bacteria were incubated at 37° C. for 12 hours and then washed 3 times with phosphate buffer (0.05 M, pH 7.5) by centrifugation at 13,000×g for 2 min at room temperature.

A biotine-alkyne probe of following formula 4 was used:

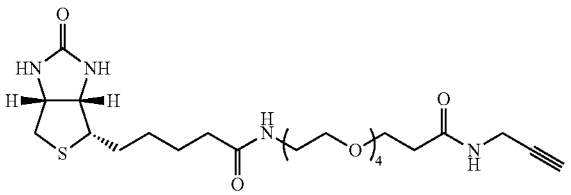

Biotin labelling was then visualized by recognition with a fluorescently labelled anti-biotin antibody as follows.

$CuSO_4$ and TGTA, at a final concentration of 2 mM and 4 mM respectively, were mixed overnight in phosphate buffer (0.05 M, pH 7.5) at 37° C. under vigorous shaking. Next, aminoguanidine, sodium ascorbate and biotin-alkyne (4) at a final concentration of 4 mM, 5 mM and 1 mM respectively were added to $CuSO_4$/TGTA overnight mix. Finally, bacteria were resuspended in this solution and incubated for 30 minutes at 37° C. Cells were then washed 3 times with phosphate buffer by centrifugation at 13,000×g for 2 min at room temperature before resuspension in 10 μl of phosphate buffer (0.05 M, pH 7.5) supplemented with 0.5 μl of Alexa Fluor 488-IgG fraction monoclonal mouse antibody anti-biotin (0.62 mg/ml stock, Jackson ImmunoResearch) and further analyzed by microscopy.

1.3) Fluorescence Microscopy

Bacteria were inoculated onto glass cover slips and covered with a thin (1 mm of thickness) semisolid 1% agar pad made with dilute LB (1/10 in phosphate buffer (0.05 M, pH 7.5)). Images were recorded with epifluorescence automated microscope (Nikon TE2000-E-PFS, Nikon, France) equipped with a CoolSNAP HQ 2 camera (Roper Scientific, Roper Scientific SARL, France) and a 100×/1.4 DLL objective. Excitation light was emitted by a 120 W metal halide light and signal was monitored using appropriate filters. Digital analysis and image processing were conducted by a custom automation script (Visual Basic) under Metamorph 7.5 (Molecular Devices, Molecular Devices France, France), as previously described [1].

2) Results

21.) Four different strains of *L. pneumophila* have been selected belonging to serogroup 1, and including (a) a strain isolated from one of the victims of the historical Philadelphia outbreak [10] (b) the Paris strain, which was responsible for a nosocomial epidemics at the newly constructed, modern and freshly opened Georges Pompidou Hospital in Paris in 2000 and has become endemic throughout Europe [11], (c) the Lens strain, that infected 86 people and killed 17 in the north of France during the 2003-2004 winter and was therefore accountable for the most important epidemics in this country.

These strains were grown first in the presence of compound Ia-1 and the incorporation of the azido chemical reporter into LPS was monitored in a subsequent step, using copper-catalysed azide-alkyne cycloaddition in the conditions previously described [12], with copper sulfate, sodium ascorbate, TGTA, a water-soluble tris (triazolyl) ligand for copper (I), and a biotine-alkyne probe of above formula 4 instead of a fluorochrome, for 30 minutes as above disclosed.

Figure 3:
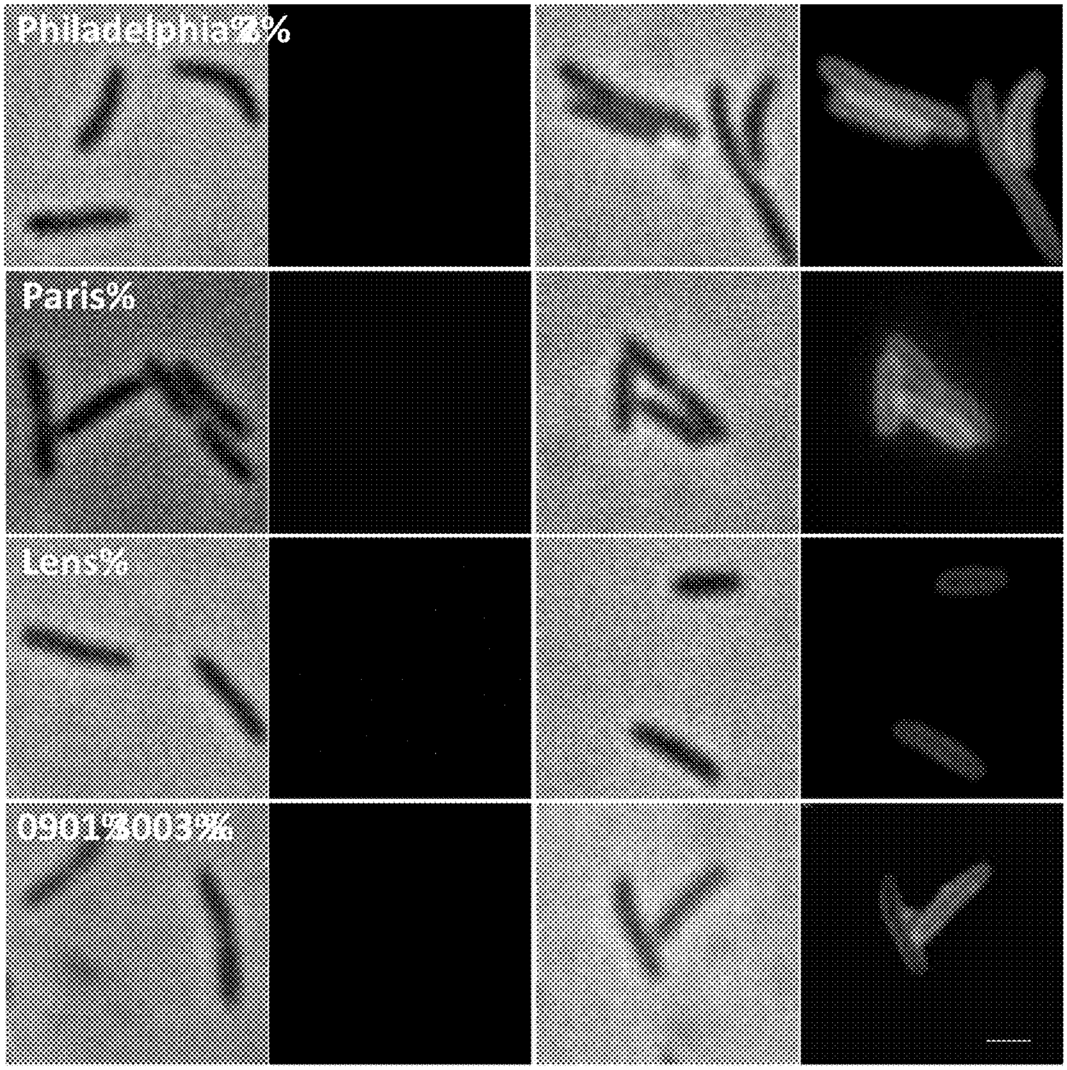
FIG. 3 represents photography of detection of metabolically incorporated compound Ia-1 by various *L. pneumophila* serogroup 1 strains.
Figure 5:
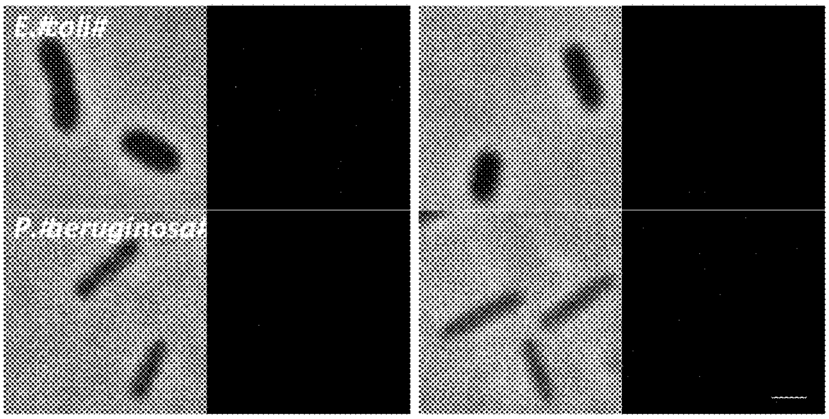
FIG. 5 represents photography of detection of metabolically incorporated compound Ia-1 by *E. coli* and *P. aeruginosa* (Compound Ia-1 is not incorporated by *E. coli* and *P. aeruginosa*)

Biotin labelling was then visualized by recognition with a fluorescently labelled anti-biotin antibody. In these experiments, all strains showed highly distinctive fluorescence on their membrane, indicative of an effective metabolic incorporation of the chemical reporter (FIG. 3). Those results are in contrast with other bacteria such as *E. coli* and *P. aeruginosa*, which both failed to show any labelling in the same conditions (FIG. 5).

This result led to test the specificity of this labeling strategy towards other strains of *Legionella*, which did not belong to the *pneumophila* species, and have therefore not been described to contain Legionaminic acid within their LPS. A representative set of such strains, containing *L. gormanii, L. maceachernii, L. micdadei, L. anisa, L. feeli, L. jordanis, L. tucsonensis and L. bozemanii* were therefore subjected to the same labelling conditions, and no membrane fluorescence was observed (FIG. 6), which is consistent with the absence of Leg within their lipopolysaccharides. The method is therefore able to efficiently discriminate between *L. pneumophila* serogroup 1 and other *Legionella*, not belonging to the *pneumophila* species.

Figure 4:
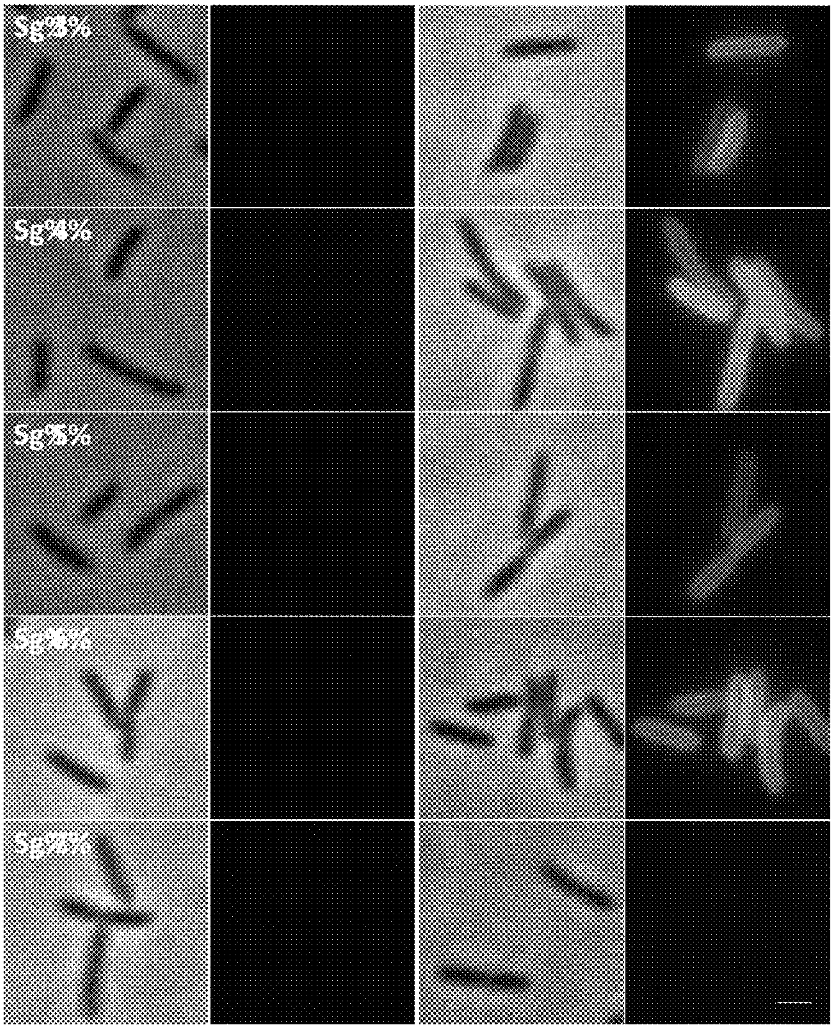
FIG. 4 represents photography of detection of metabolically incorporated compound Ia-1 by various *L. pneumophila* strains belonging to other serogroups than serogroup 1.

The capacity of this method to label *L. pneumophila* strains belonging to other serogroups was then evaluated. This is an interesting point, since although serogroup 1 is found in most infected cases, other serogroups are abundant in the environment. The possibility to label these other serogroups would therefore be an important result allowing a better evaluation of the presence of *L. pneumophila* in a given sample. Most of these serogroups have been shown to contain another isomer of a 5-acetamidino-7-acetamido-3,5,7,9-tetradeoxynon-2-ulosonic acid, namely 5-N-acetimidoyl-7-N-acetyl-4-epi-legionaminic acid (4eLeg5Am7Ac) [13], with various degrees of 8-O-acetylation depending on the serogroup. Contrary to the Leg pathway, the 4eLeg biosynthetic pathway has not been identified yet, but one could speculate that it might involve similar intermediates. Four strains, belonging to serogroups 3, 4, 5, 6, which represent together with serogroup 1 between 68 and 85% of the *L. pneumophila* present in the environment [1], showed very bright membrane labelling (FIG. 4). This tends to indicate that Leg and 4eLeg biosynthesis apparently share Ia as a common precursor. However it cannot be concluded at this point if Leg and 4eLeg are directly obtained from the modification of this common precursor, for example by two different aldolases, or if Leg is produced in all strains and further converted into 4eLeg by an epimerase at a later stage of the pathway. Nevertheless, this method allows clear specific detection of *L. pneumophila* strains that do not belong to serogroup 1.

Interestingly, the only exception observed concerned a *L. pneumophila* strain belonging to serogroup 7 (FIG. 4), a serogroup which is very poorly represented both in infection cases and in the environment. Serogroup 7 has been described to present a still unidentified isomer of 5-acetamidino-7-acetamido-3,5,7,9-tetradeoxynon-2-ulosonic acid within its O-polysaccharide [13]. This observation is consistent with the absence of labelling, which tends to indicate that compound Ia is not an intermediate in the corresponding biosynthetic pathway. An isomer of Ia is most certainly involved as a substrate for the aldolase.

Another set of experiments was performed using Ia-1', a mono-acetylated derivative of Ia-1 wherein R2 is —OAc. It was expected that this less polar esterified compound might enter the bacterial cell more efficiently via passive transport, and could be further incorporated into the LPS after deacetylation to Ia-1 by non-specific esterase activity within the cell. The availability and extent of such an activity inside bacterial cells has been the subject of recent debate within the scientific community [14]. No labelling was observed in the laboratory in vitro conditions with Ia-1', even in the case of the *L. pneumophila* strains that were efficiently labelled by 2 (FIG. 7). This suggests that such an esterase activity is not present at a sufficient level within the bacterial cell to allow efficient production of Ia-1 from Ia-1' and further metabolisation and incorporation of Ia-1 to a detectable proportion.

The above method appears as an efficient strategy to specifically detect and identify living *L. pneumophila*, a pathogenic bacterium of high sanitary and economical impact. The absence of labeling with an acetylated precursor in the above laboratory conditions can be explained by the fact that non-specific esterase activity within such *Legionella* bacteria might not be sufficient for the efficient liberation inside the bacterial cell of a previously acetylated carbohydrate precursor. However such non-specific esterase are present and metabolization and incorporation with Ia-1' could therefore occur in eukaryotic cells environment such as in the circumstances which occur in the refrigerant tower wherein *legionella* can be carried within amibes or in biological sample comprising eukaryotic cells such as human samples.

2.2) In order to test the incorporation of Ib-1, four different strains of *L. pneumophila* have been selected from Table 1 (see Table 2).

TABLE 2

| *Legionella* species | Serogroup | Type |
|---|---|---|
| *Legionella pneumophila* | | |
| Philadelphia 2 | 1 | 33152 |
| Paris | 1 | CIP 33152 |
| | 3 | LG 0903 1009 |
| | 6 | LG 0846 3022 |

The same experimental proceedings have been carried out as above mentioned. These strains were grown first in the presence of compound Ib-1 and the incorporation of the azido chemical reporter into LPS was monitored in a subsequent step, using copper-catalysed azide-alkyne cycloaddition in the conditions previously described and a biotine-alkyne probe of above formula 4 instead of a fluorochrome, for 30 minutes as above disclosed. Biotin labelling was then visualized by recognition with a fluorescently labelled anti-biotin antibody. In these experiments, all strains showed highly distinctive fluorescence on their membrane, indicative of an effective metabolic incorporation of the chemical reporter. These results indicated as expected that compound Ib-1 is also assimilated by *L. pneumophila.*"

BIBLIOGRAPHY REFERENCES

[1] Yu, V. L. et al. Distribution of *Legionella* Species and Serogroups Isolated by Culture in Patients with Sporadic Community-Acquired Legionellosis: An International Collaborative Survey. J. Infect. Dis. 186, 127-128 (2002); Doleans, A. et al. Clinical and Environmental Distributions of *Legionella* Strains in France Are Different. J. Clin. Microbiol. 42, 458-460 (2004); Harrison, T. G., Afshar, B., Doshi, N., Fry, N. K. & Lee, J. V. Distribution of *Legionella pneumophila* serogroups, monoclonal antibody subgroups and DNA sequence types in recent clinical and environmental isolates from England and Wales (2000-2008). Eur. J. Clin. Microbiol. Infect. Dis. 28, 781-791 (2009).

[2] Knirel, Y. A., Rietschel, E. T., Marre, R. & Zahringer, U. The structure of the O-specific chain of *Legionella pneumophila* serogroup 1 lipopolysaccharide. Eur. J. Biochem. 221, 239-245 (1994).

[3] Glaze, P. A., Watson, D. C., Young, N. M. & Tanner, M. E. Biosynthesis of CMP-N,N'-diacetyllegionaminic acid from UDP-N,N'-diacetylbacillosamine in *Legionella pneumophila*. Biochemistry 47, 3272-3282 (2008).

[4] McGill, N. W. & Williams, S. J. 2,6-Disubstituted Benzoates As Neighboring Groups for Enhanced Diastereoselectivity in β-Galactosylation Reactions: Synthesis of β-1,3-Linked Oligogalactosides Related to Arabinogalactan Proteins. J. Org. Chem. 74, 9388-9398 (2009).

[5] Zemplén, G., Kunz, A. Über die Natriumverbindungen der Glucose and die Verseifung der acylierten Zucker. Chem Ber 56, 1705-1710 (1923).

[6] Lee, D. & Taylor, M. S. Borinic Acid-Catalyzed Regioselective Acylation of Carbohydrate Derivatives. J. Am. Chem. Soc. 133, 3724-3727 (2011).

[7] Tsvetkov, Y. E., Shashkov, A. S., Knirel, Y. A. & Zahringer, U. Synthesis and NMR spectroscopy of nine stereoisomeric 5,7-diacetamido-3,5,7,9-tetradeoxynon-2-ulosonic acids. Carbohydr Res 335, 221-243 (2001).

[8] Dumont, A., Malleron, A., Awwad, M., Dukan, S. & Vauzeilles, B. Click-mediated labeling of bacterial membranes through metabolic modification of the lipopolysaccharide inner core. Angew. Chem. Int. Ed. Engl. 51, 3143-3146 (2012).

[9] Hewitt, M. C. & Seeberger, P. H. Solution and Solid-Support Synthesis of a Potential Leishmaniasis Carbohydrate Vaccine. J. Org. Chem. 66, 4233-4243 (2001).

[10] Moss, C. W., Weaver, R. E., Dees, S. B. & Cherry, W. B. Cellular fatty acid composition of isolates from Legionnaires disease. J. Clin. Microbiol. 6, 140-143 (1977).

[11] Aurell, H. et al. *Legionella pneumophila* Serogroup 1 Strain Paris: Endemic Distribution throughout France. J. Clin. Microbiol. 41, 3320 (2003).

[12] Baron, A., Bleriot, Y., Sollogoub, M. & Vauzeilles, B. Phenylenediamine catalysis of "click glycosylations" in water: practical and direct access to unprotected neoglycoconjugates. Org. Biomol. Chem. 6, 1898-1901 (2008).

[13] Knirel, Y. A. et al. Identification of a Homopolymer of 5-Acetamidino-7-acetamido-3,5,7,9-tetradeoxy-d-glycero-d-talo-nonulosonic Acid in the Lipopolysaccharides of *Legionella pneumophila* Non-1 Serogroups. Biochemistry (Moscow) 66, 1035-1041 (2001).

[14] Antonczak, A. K., Simova, Z. & Tippmann, E. M. A critical examination of *Escherichia coli* esterase activity. J. Biol. Chem. 284, 28795-28800 (2009).

The invention claimed is:

1. A method for labeling specifically living bacteria of a given category of bacteria in a sample comprising bacteria, the method comprising the steps of:

a) incubating said bacteria of said sample with at least one modified monosaccharide compound comprising a first reactive chemical group capable to chemically react with a second reactive group, so that a monosaccharide residue bearing said first reactive group is incorporated into a polysaccharide of an outer membrane of said bacteria, and b) contacting said modified monosaccharide residue incorporated within the outer membrane of the bacteria, with a labeling molecule comprising said second reactive group, for generating the chemical reaction of said first reactive group of said monosaccharide residue incorporated within said outer membrane of said living bacteria with said second reactive group of said labeling molecule, resulting in a covalent link, wherein said modified monosaccharide compound is a modified endogenous precursor of an endogenous ulosonic acid residue of said polysaccharides of the outer membrane of said bacteria, said modified monosaccharide compound having the following formula (I), or a salt thereof:

I

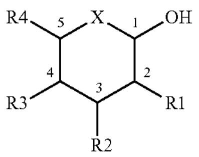

wherein,

X is O, and

R1, R2 and R3 are independently H, OH, $NH_2$, OH and $NH_2$ being substituted or not by protecting groups thereof, and R4 is H or an alkyl chain in $C_1$ to $C_4$ each carbon being substituted or not by OH or $NH_2$ substituted or not by protecting groups thereof, and at least one of R1, R2, R3 and R4 groups being substituted by said first reactive group.

2. The method according to claim 1 wherein said modified monosaccharide compound is a compound having said formula (I), or a salt thereof, wherein:

R1 is H, OH, $NH_2$, OH and $NH_2$ being substituted or not by said protecting group, and R3 is $NH_2$ substituted or not substituted by protecting group thereof;

R2 is OH substituted or not substituted by a protecting group thereof, and at least one of R1, R3 and R4 being substituted by said first reactive group.

3. The method according to claim 1, wherein said modified monosaccharide compound is a compound having one of the following formulas (Ix-1) to (Ix-4), or a salt thereof:

Ix-1

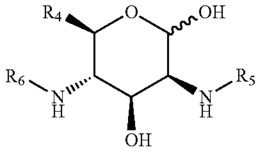

Ix-2

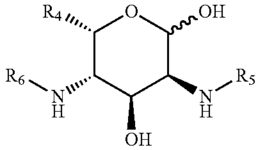

Ix-3

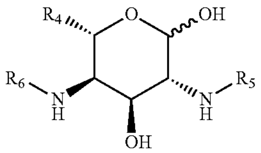

Ix-4

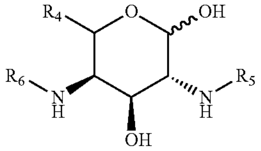

wherein

R4 is H or an alkyl chain in $C_1$ to $C_4$, each carbon being substituted or not by OH or $NH_2$ substituted or not by protecting groups thereof, and R5 and R6 are independently alkyl, hydroxyalkyl, acyl, formyl or imidoyl groups, substituted or not, and at least one of R4, R5 and R6 groups being substituted by said first reactive group.

4. The method according to claim 1, wherein said modified monosaccharide compound is a compound having said formula (I), or a salt thereof wherein:

R1 and R3 are $NH_2$ substituted or not substituted by a protecting group thereof, and R2 is OH substituted or not substituted by a protecting group thereof, and R4 is substituted by said first reactive group.

5. The method according to claim 1, wherein said modified monosaccharide compound is selected from the group consisting of the following compounds Ia and Ib:

compound Ia being a compound having the formula (I) wherein R1 and R3 are —NHAc, R2 is —OAc or OH and R4 is $CH_2$—Ra; and compound Ib being a compound having the formula (I) wherein R1 and R3 are —$NHCOCH_2Ra$, R2 is —OAc or OH, and R4 is $CH_2OH$.

6. The method according to claim 1, wherein said bacteria are Gram negative bacteria, comprising an endogenous monosaccharide residue within a lipopolysaccharide layer of an outer membrane of the Gram negative bacteria.

7. The method according to claim 1, wherein said modified monosaccharide compound is a compound having one the following formula (Ia-1), (Ia-1'), (Ib-1) or a salt thereof:

(Ia-1)

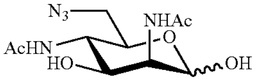

-continued (Ia-1')

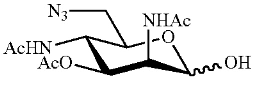

(Ib-1)

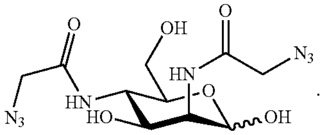

8. The method according to claim 7, for labeling specifically living *Legionella pneumophila* bacteria, and said modified monosaccharide compound is a compound of formula Ia-1.

9. The method according to claim 1, comprising the further step of:

c) detecting living bacteria in detecting whether said bacteria comprise said labeling molecule bound to the glycans of their outer membrane and/or immobilizing said living bacteria bearing said labeling molecule onto a solid substrate, wherein said labeling molecule is a molecule comprising a detectable substance or capable to react or to be bound to a detectable substance or said labeling molecule is a first molecule bearing said second reactive group, said first molecule being capable to react or to be bound to a second molecule and/or to a solid substrate.

10. The method according to claim 9 for specifically detecting living bacteria of a given category of bacteria in a sample comprising bacteria, wherein said labeling molecule is a detectable molecule comprising a detectable substance, the method comprising the step c) of detecting living bacteria in detecting whether said bacteria comprise said detectable molecule bound to the glycans of their outer membrane.

11. The method according to claim 9, wherein said labeling molecule is a first ligand or first binding protein bearing said second reactive group and in step c) said living bacteria coupled to said first ligand or first binding protein is detected and/or immobilized by contacting said first ligand or first binding protein with a second ligand or second binding protein reacting or binding specifically to said first ligand or first binding protein.

12. The method according to claim 9, wherein said labeling molecule is a first ligand bearing said second reactive group, and in step c) said living bacteria coupled to said first ligand are detected by reaction of said bacteria with an antibody specific to said first ligand, said antibody bearing a detectable substance.

13. The method according to claim 1, wherein the first reactive group is selected from the group consisting of azido-comprising groups and alkyne-comprising groups, and the second reactive group is selected from the group consisting of alkyne-comprising groups and azido-comprising groups.

14. A kit for carrying out the method of claim 1, said kit comprising:

said modified monosaccharide compound of formula (I) substituted by said first reactive group, said compound of formula I being a modified precursor able to be converted into a modified endogenous ulosonic acid residue incorporated into a polysaccharide of the outer membrane of a bacteria, and said labeling molecule comprising said second reactive group capable of reacting with said first reactive group, and optionally, reactants for generating the reaction of said first reactive group of said analog residue incorporated within said polysaccharides of the outer membrane of said bacteria with said second reactive group of said labeling molecule, said compound, or a salt thereof, having the formula:

I

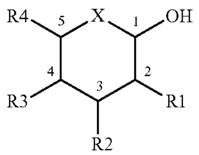

wherein,

X is O, and

R1, R2 and R3 are independently H, OH, $NH_2$, OH and $NH_2$, being substituted or not by protecting groups thereof, and R4 is H or an alkyl chain in $C_1$ to $C_4$, each carbon being substituted or not by OH or $NH_2$, substituted or not by protecting groups thereof, and at least one of R1, R2, R3, and R4 groups being substituted by said first reactive group.

15. The kit according to claim 14, further comprising a culture or incubation medium allowing the growth of said given category of bacteria.

16. The method according to claim 1, wherein R1, R2, and R3 are, independently, H, OH, $NH_2$, OH, and $NH_2$, being substituted by alkyl, hydroxyalkyl, acyl, formyl or imidoyl groups.

17. The method according to claim 1, wherein R4 is an alkyl chain in C1 to C4, each carbon being substituted by OH or $NH_2$ substituted by protecting groups thereof selected from the group consisting of alkyl, hydroxyalkyl, acyl, formyl and imidoyl groups.

18. The method according to claim 1, wherein said modified monosaccharide compound is a compound having the formula (I), or a salt thereof, wherein:

R1 and R3 are $NH_2$ substituted or not substituted by a protecting group thereof, and R2 is OH substituted or not substituted by a protecting group thereof, and R4 is substituted by said first reactive group, R4 being $CH_3$, $—CH_2OH$ or $—CH_2NH_2$, or said first reactive group Ra being $N_3$.

19. The method according to claim 1, wherein said bacteria are Gram negative bacteria comprising an endogenous monosaccharide residue within the lipopolysaccharides layer of an outer membrane of the Gram negative bacteria which are selected from the group consisting of *Legionella pneumophila, Vibrio alginolyticus, Acinetobacter baumannii, Pseudomonas fluorescens, Vibrio salmonicida, Tenacibaculum maritimum, Escherichia coli, Salmonella typhymurium, Schewanella japonica, Providencia stuartii, Pseudomonas aeruginosa, Yersinia ruckeri, Salmonella arizonae, Morganella morganii, Shewanella putrefaciens, Shigella boydii, Proteus vulgaris, Pseudoalteromonas atlantica, Pseudoalteromonas distincta, Sinorhizobium fredii, vibrio cholerae, Pseudoalteromonas atlantica, Vibrio parahaemolyticus, Campylobacter jejuni, Campylobacter coli, Clostridium botulinum*, and *Yersinia enterocolitica.*

20. The method according to claim 1, further comprising the step of:

c) detecting living bacteria in detecting whether said bacteria comprise said labeling molecule bound to the glycans of their outer membrane and/or immobilizing said living bacteria bearing said labeling molecule onto a solid substrate, wherein said labeling molecule is a molecule comprising a detectable substance or capable to react or to be bound to a detectable substance or said labeling molecule is a first molecule bearing said second reactive group, said first molecule being capable to react or to be bound to a second molecule and/or to a solid substrate, and said second molecule comprising a detectable substance and/or said second molecule being bound or capable to be bound to said solid substrate.

21. The method according to claim 9, wherein said labeling molecule is a first ligand that is biotin, bearing said second reactive group, and in step c) said living bacteria coupled to said first ligand are detected by reaction of said bacteria with an antibody specific to said first ligand, said antibody bearing a detectable substance that is a fluorochrome or luminescent molecule or an enzyme.

22. The method according to claim 1, wherein the first reactive group is the group azido, and the said second reactive group is the group alkyne, reacting the said azido reactive group with the said alkyne reactive group is carried out in performing an azide alkyne cycloaddition.

23. The kit according to claim 14, further comprising a culture or incubation medium allowing the growth of said given category of bacteria specific to the growth of said given category of bacteria.

24. The method according to claim 1, wherein the polysaccharide is a lipopolysaccharide or a capsular polysaccharide.

25. The kit according to claim 14, wherein the polysaccharide is a lipopolysaccharide or a capsular polysaccharide.

* * * * *